US011841315B2

(12) United States Patent
Haji Reza et al.

(10) Patent No.: US 11,841,315 B2
(45) Date of Patent: Dec. 12, 2023

(54) PHOTOACOUSTIC REMOTE SENSING (PARS), AND RELATED METHODS OF USE

(71) Applicant: ILLUMISONICS INC., Edmonton (CA)

(72) Inventors: Parsin Haji Reza, Edmonton (CA); Kevan Bell, Edmonton (CA)

(73) Assignee: ILLUMISONICS INC., Waterloo (CA)

( * ) Notice: Subject to any disclaimer, the term of this patent is extended or adjusted under 35 U.S.C. 154(b) by 791 days.

(21) Appl. No.: 16/629,371

(22) PCT Filed: Dec. 19, 2019

(86) PCT No.: PCT/IB2019/061131
§ 371 (c)(1),
(2) Date: Jan. 8, 2020

(87) PCT Pub. No.: WO2021/123893
PCT Pub. Date: Jun. 24, 2021

(65) Prior Publication Data
US 2021/0404948 A1     Dec. 30, 2021

(51) Int. Cl.
*G01N 21/17*     (2006.01)
*A61B 5/00*     (2006.01)

(52) U.S. Cl.
CPC ........ *G01N 21/1702* (2013.01); *A61B 5/0095* (2013.01); *G01N 2021/1706* (2013.01); *G01N 2201/06113* (2013.01)

(58) Field of Classification Search
CPC ....... G01N 21/1702; G01N 2021/1706; G01N 2201/06113; A61B 5/0095;
(Continued)

(56) References Cited

U.S. PATENT DOCUMENTS

| 5,070,733 A | 12/1991 | Nagata et al. |
| 5,479,259 A | 12/1995 | Nakata et al. |

(Continued)

FOREIGN PATENT DOCUMENTS

| CN | 101526483 A | 9/2009 |
| CN | 103048271 A | 4/2013 |

(Continued)

OTHER PUBLICATIONS

Adhikari et al., "Photothermal Microscopy: Imaging the Optical Absorption of Single Nanoparticles and Single Molecules," ACS Nano 2020, 14 (12), 16414-16445 (32 pages).

(Continued)

*Primary Examiner* — Suman K Nath
(74) *Attorney, Agent, or Firm* — Bookoff McAndrews, PLLC

(57) ABSTRACT

A photoacoustic remote sensing system (PARS) for imaging a subsurface structure in a sample, comprising one or more laser sources configured to generate a plurality of excitation beams configured to generate pressure signals in the sample at an excitation location, and a plurality of interrogation beams incident on the sample at the excitation location, a portion of the plurality of interrogation beams returning from the sample that is indicative of the generated pressure signals, an optical system configured to focus the plurality of excitation beams at a first focal point and the plurality of interrogation beams at a second focal point, the first and second focal points being below the surface of the sample, and a plurality of detectors each configured to detect a returning portion of at least one of the plurality of interrogation beams.

20 Claims, 8 Drawing Sheets

(58) Field of Classification Search
CPC ............ A61B 5/14546; A61B 5/14552; A61B 5/0261; A61B 2503/40
See application file for complete search history.

(56) References Cited

U.S. PATENT DOCUMENTS

| | | | |
|---|---|---|---|
| 5,615,675 | A | 4/1997 | O'Donnell et al. |
| 5,991,479 | A | 11/1999 | Kleinerman |
| 6,016,202 | A | 1/2000 | Fuchs et al. |
| 6,078,397 | A | 6/2000 | Monchalin et al. |
| 6,256,100 | B1 | 7/2001 | Banet et al. |
| 6,973,830 | B2 | 12/2005 | Pepper et al. |
| 6,992,829 | B1 | 1/2006 | Jennings et al. |
| 7,068,842 | B2 | 6/2006 | Iang et al. |
| 8,004,689 | B2 | 8/2011 | Monchalin et al. |
| 8,180,134 | B2 | 5/2012 | Wang |
| 8,454,512 | B2 | 6/2013 | Wang et al. |
| 8,692,155 | B2 | 4/2014 | Bischoff et al. |
| 9,153,931 | B2 | 10/2015 | Ichihara et al. |
| 9,999,354 | B2 | 6/2018 | Rousseau et al. |
| 2006/0184042 | A1 | 8/2006 | Wang et al. |
| 2006/0262316 | A1 | 11/2006 | Baney |
| 2008/0123083 | A1 | 5/2008 | Wang et al. |
| 2008/0194929 | A1 | 8/2008 | Pesach et al. |
| 2009/0170149 | A1 | 7/2009 | Viator et al. |
| 2010/0268042 | A1 | 10/2010 | Wang et al. |
| 2012/0200845 | A1 | 8/2012 | Rousseau et al. |
| 2012/0320368 | A1 | 12/2012 | Jiao et al. |
| 2014/0009808 | A1 | 1/2014 | Wang et al. |
| 2014/0118749 | A1 | 5/2014 | Nakajima et al. |
| 2014/0185055 | A1 | 7/2014 | Wang |
| 2014/0247456 | A1 | 9/2014 | Horstmann et al. |
| 2015/0077819 | A1 | 3/2015 | Schnell et al. |
| 2015/0148655 | A1 | 5/2015 | Haupt et al. |
| 2015/0150465 | A1 | 6/2015 | Irisawa et al. |
| 2015/0153269 | A1 | 6/2015 | Nakatsuka |
| 2015/0164337 | A1 | 6/2015 | Kim et al. |
| 2015/0185187 | A1 | 7/2015 | Wang et al. |
| 2015/0221081 | A1 | 8/2015 | Chang et al. |
| 2015/0265156 | A1 | 9/2015 | Tanaka |
| 2016/0113507 | A1 | 4/2016 | Reza et al. |
| 2017/0084773 | A1* | 3/2017 | Piccione ............. H01L 31/1075 |
| 2017/0215738 | A1 | 8/2017 | Reza et al. |

FOREIGN PATENT DOCUMENTS

| | | |
|---|---|---|
| CN | 109363639 A | 2/2019 |
| DE | 10 2010 012 809 A1 | 9/2011 |
| WO | 2009055705 A2 | 4/2009 |
| WO | 2009055705 A3 | 6/2009 |
| WO | 2013023210 A1 | 2/2013 |
| WO | 2013166044 A1 | 11/2013 |
| WO | 2014027316 A2 | 2/2014 |
| WO | 2014036405 A2 | 3/2014 |
| WO | 2014062529 A1 | 4/2014 |
| WO | 2014160116 A1 | 10/2014 |
| WO | 2014168930 A1 | 10/2014 |
| WO | 2019145764 A1 | 8/2019 |
| WO | 2019170884 A1 | 9/2019 |

OTHER PUBLICATIONS

Tavakolian et al., "Perspective: Principles and specifications of photothermal imaging methodologies and their applications to non-invasive biomedical and non-destructive materials imaging," J. Appl. Phys. 124, 160903 (2018) (13 pages).
Beard, Paul. "Biomedical Photoacoustic Imaging." Interface Focus 1.4 (2011): 602-631. PMC. Web. Dec. 12, 2017.
International Search Report and Written Opinion dated Dec. 19, 2018 in International Application No. PCT/IB2018/057585 (25 pages).
Kevan L. Bell et al., "Coherence-gated photoacoustic remote sensing microscopy", Optics Express, vol. 26, No. 18, Sep. 3, 2018, 16 pp.
Zhihua Ding et al., "Real-time phase-resolved optical coherence tomography and optical Doppler tomography", Optics Express, vol. 10, No. 5, Mar. 11, 2002, 10 pages.
Cedric Blatter et al., "Intrasweep phase-sensitive optical coherence tomography for noncontact optical photoacoustic imaging", Optics Letters, vol. 37, No. 21, Nov. 1, 2012, 4 pp.
Fu, Yu et al., "Photo-vibrational Sensing of Trace Chemicals and Explosives by Long-Distance Differential Laser Doppler Vibrometer", Chemical, Biological, Radiological, Nuclear, and Explosives (CBRNE) Sensing XVIII, vol. 10183, 101830B (May 2017).
Extended European Search Report in PCT/IB2019061131, dated Sep. 15, 2023 (9 pages).

* cited by examiner

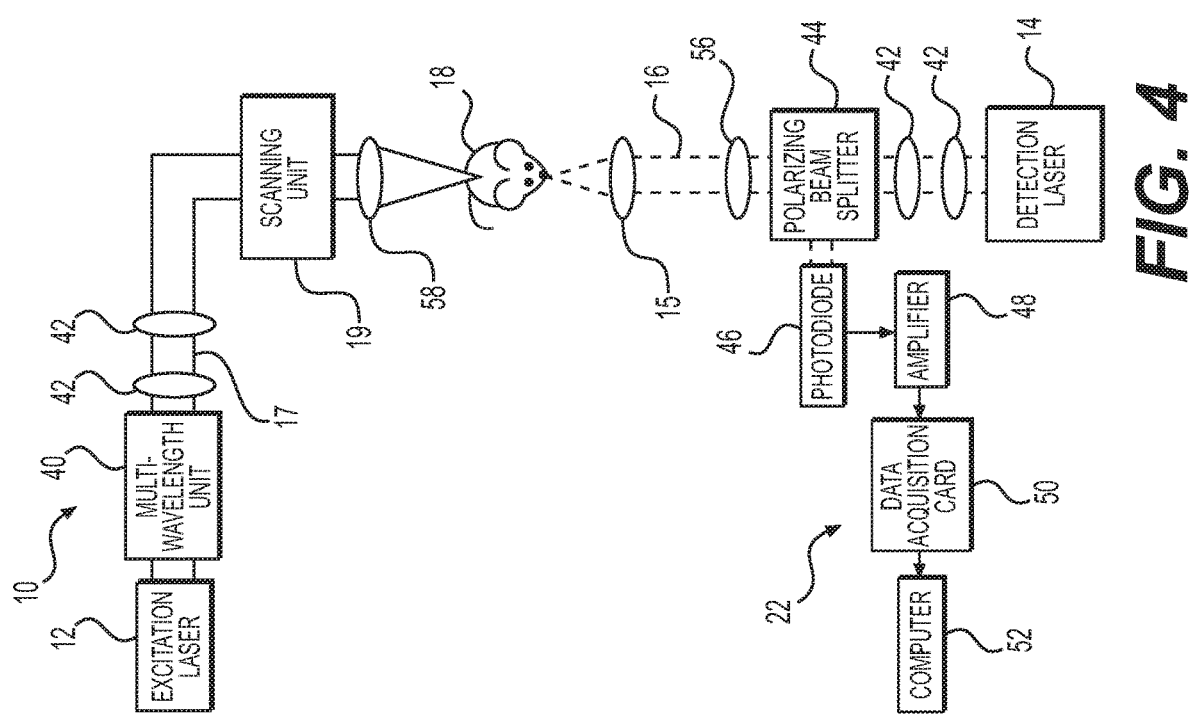

PHOTOACOUSTIC REMOTE SENSING (PARS), AND RELATED METHODS OF USE

CROSS-REFERENCE TO RELATED APPLICATION(S)

This patent application is the U.S. national phase entry under 35 U.S.C. § 371 of International Application No. PCT/IB2019/061131, filed Dec. 19, 2019.

FIELD

This application relates to the field of biomedical optics imaging and, in particular, to a laser and ultrasound-based method and system for in vivo or ex vivo, non-contact imaging of biological tissue.

BACKGROUND

Photoacoustic imaging is an emerging hybrid imaging technology providing optical contrast with high spatial resolution. Nanosecond or picosecond laser pulses fired into tissue launch thermo-elastic-induced acoustic waves which are detected and reconstructed to form high-resolution images. Photoacoustic imaging has been developed into multiple embodiments, including photoacoustic tomography (PAT), photoacoustic microscopy (PAM), optical-resolution photoacoustic microscopy (OR-PAM), and array-based PA imaging (array-PAI). In photoacoustic tomography (PAT), signals are collected from multiple transducer locations and reconstructed to form a tomographic image in a way similar to X-ray CT. In PAM, typically, a single element focused high-frequency ultrasound transducer is used to collect photoacoustic signals. A photoacoustic signal as a function of time (depth) is recorded for each position in a mechanically scanned trajectory to form a 3-D photoacoustic image. The maximum amplitude as a function of depth can be determined at each x-y scan position to form a maximum amplitude projection (MAP) C-scan image. Photoacoustic microscopy has shown significant potential for imaging vascular structures from macro-vessels all the way down to micro-vessels. It has also shown great promise for functional and molecular imaging, including imaging of nanoparticle contrast agents and imaging of gene expression. Multi-wavelength photoacoustic imaging has been used for imaging of blood oxygen saturation, by using known oxy- and deoxy-hemoglobin molar extinction spectra.

In traditional photoacoustic imaging, spatial resolution is due to ultrasonic focusing and can provide a depth-to-resolution ratio greater than 100. In OR-PAM, penetration depth is limited to ~1 mm in tissue (due to fundamental limitations of light transport) but resolution is micron-scale due to optical focusing. OR-PAM can provide micron-scale images of optical absorption in reflection-mode, in vivo, something that no other technique can provide. OR-PAM is capable of imaging blood vessels down to capillary size noninvasively. Capillaries are the smallest vessels in the body and much crucial biology occurs at this level, including oxygen and nutrient transport. Much can go wrong at the capillary level too. In cancers, cells have an insatiable appetite for oxygen and nutrients to support their uncontrolled growth. They invoke a range of signaling pathways to spawn new vessels in a process known as angiogenesis and these vessels typically form abnormally. Tumors are often highly heterogeneous and have regions of hypoxia. Photoacoustic imaging has demonstrated the ability to image blood oxygen saturation (SO2) and tumor hypoxia in vivo.

In most photoacoustic and ultrasound imaging systems, piezoelectric transducers have been employed, in which an ultrasound coupling medium such as water or ultrasound gel is required. However, for many clinical applications such as wound healing, burn diagnostics, surgery, and many endoscopic procedures, physical contact, coupling, or immersion is undesirable or impractical.

The detection of ultrasound in photoacoustic imaging has, until recently, relied on ultrasonic transducers in contact with the biological tissue or an ultrasonic coupling agent both of which have major drawbacks as described above. Some detection strategies to solving the non-contact optical interferometric sensing problems associated with photoacoustic imaging have been reported.

Optical means of detecting ultrasound and photoacoustic signals have been investigated over a number of years; however, to date, no technique has demonstrated practical non-contact in vivo microscopy in reflection mode with confocal resolution and optical absorption as the contrast mechanism.

Most previous approaches detected surface oscillations with interferometric methods. Others used interferometry to observe photoacoustic stresses, including optical coherence tomography (OCT) methods. These methods offer potential sensitivity to the scattered probe beam phase modulations associated with motion of scatterers, subsurface and surface oscillations, as well as unwanted vibrations. They are also sensitive to complex amplitude reflectivity modulations.

One example of a low-coherence interferometry method for sensing photoacoustic signals was proposed in U.S. pregnant publication no. 2014/0185055 to be combined with an optical coherence tomography (OCT) system, resulting in 30 µm lateral resolution.

Another prior art system is described in U.S. pregnant publication no. 2012/0200845 entitled "Biological Tissue Inspection Method and System", which describes a noncontact photoacoustic imaging system for in vivo or ex vivo, non-contact imaging of biological tissue without the need for a coupling agent.

Other systems use a fiber based interferometer with optical amplification to detect photoacoustic signals and form photoacoustic images of phantoms with acoustic (not optical) resolution. However, these systems suffer from a poor signal-to-noise ratio, whereas other contact-based photoacoustic systems offer significantly improved detection capabilities. Furthermore, in vivo imaging was not demonstrated, and optical-resolution excitation was not demonstrated.

Industrial laser ultrasonics has used interferometry to detect acoustic signatures due to optical excitation of inanimate objects for non-destructive testing. This approach has been adapted to detect ultrasound ex vivo in chicken breast and calf brain specimens, however, optical-resolution focusing of the excitation light was not examined.

Laser Doppler vibrometry has been a powerful non-contact vibration sensing methodology, however, weak signal-to-noise and poor image quality have proven to be a limitation when sensing deep-tissue signals from broad-beam photoacoustic excitation.

Similarly, Mach Zehnder interferometry and two-wave mixing interferometry have been used previously for sensing photoacoustic signals. However, many such techniques still require direct contact or fluid coupling; they have not offered in vivo studies or optical resolution for phantom studies.

The photoacoustic remote sensing (PARS) (including the non-interferometric photoacoustic remote sensing (NI-PARS)) systems described herein are fundamentally different from other approaches for detection ultrasound/photoacoustic signals. The PARS takes advantage of a excitation beam co-focused and co-scanned with an interrogation beam. Specifically, the PARS uses nJ-scale pulse energies focused to near diffraction-limited spots, and not the conventional broad excitation beams delivered over broad areas. Furthermore, in the NI-PARS, the detection mechanism is based on a non-interferometric sensing. Rather than detecting surface oscillations, pressure-induced refractive-index modulation resulting from initial pressure fronts can be sampled right at their subsurface origin where acoustic pressures are large. The non-interferometric nature of detection along with the short-coherence lengths of the interrogation laser preclude detection of surface and sub-surface oscillations to provide only the initial pressure signals.

SUMMARY

According to an example, a photoacoustic remote sensing system (PARS) for imaging a subsurface structure in a sample may comprise one or more laser sources configured to generate a plurality of excitation beams configured to generate pressure signals in the sample at an excitation location, and a plurality of interrogation beams incident on the sample at the excitation location, a portion of the plurality of interrogation beams returning from the sample that is indicative of the generated pressure signals. The PARS may further comprise an optical system configured to focus the plurality of excitation beams at a first focal point and the plurality of interrogation beams at a second focal point, the first and second focal points being below the surface of the sample, and a plurality of detectors each configured to detect a returning portion of at least one of the plurality of interrogation beams. The one or more laser sources may be a plurality of laser sources. Each of the plurality of excitation beams may have a different wavelength. The plurality of excitation beams may include a near-infrared beam, a short-wave infrared beam, a UVC beam, a UVB beam, a UVA beam, and visible light. The plurality of excitation beams may be configured to be delivered sequentially onto the sample, or the plurality of excitation beams may be configured to be delivered simultaneously onto the sample. The first and second focal points may be at a depth below the surface of the sample that is less than 1 µm.

In another example, a photoacoustic remote sensing system (PARS) for imaging a subsurface structure in a sample may comprise one or more laser sources configured to generate at least one excitation beam configured to generate ultrasonic signals in the sample at an excitation location, wherein the at least one excitation beam is directed to the sample along a first path, and at least one interrogation beam incident on the sample at the excitation location and directed to the sample along a second path that is offset from the first path, at least one portion of the at least one interrogation beam returning from the sample that is indicative of the generated ultrasonic signals, wherein the returning portion of the at least one interrogation beam returns along a third path that is offset from each of the first path and the second path. The PARS may further include a first optical system configured to focus the at least one excitation beam at a first focal point, a second optical system configured to focus the at least one interrogation beam at a second focal point, the first and second focal points being below the surface of the sample, and at least one detector configured to detect at least one returning portion of the at least one interrogation beam. The angle between the first path and second path may be substantially similar to an angle between the second path and the third path. The angle between the first path and the third path may be substantially similar to an angle between the first path and the third path.

In another example, a photoacoustic remote sensing system (PARS) for imaging a subsurface structure in a sample may comprise one or more laser sources configured to generate at least one excitation beam configured to generate ultrasonic signals in the sample at an excitation location, and at least one interrogation beam incident on the sample at the excitation location, at least one portion of the at least one interrogation beam returning from the sample that is indicative of the generated ultrasonic signals. The PARS may further comprise an optical system configured to focus the at least one excitation beam at a first focal point and the at least one interrogation beam at a second focal point, the first and second focal points being below the surface of the sample, and a polarizing modulation detector configured to detect a polarization modulation of the at least one returning portion.

According to another example, a photoacoustic remote sensing system (PARS) for imaging a subsurface structure in a sample may comprise one or more laser sources configured to generate at least one excitation beam configured to generate ultrasonic signals in the sample at an excitation location, and at least one interrogation beam incident on the sample at the excitation location, at least one portion of the at least one interrogation beam returning from the sample that is indicative of the generated ultrasonic signals. The PARS may further comprise an optical system configured to focus the at least one excitation beam at a first focal point and the at least one interrogation beam at a second focal point, the first and second focal points being below the surface of the sample, and a phase modulation detector configured to detect a phase modulation of the at least one returning portion.

In another example, a photoacoustic remote sensing system (PARS) for imaging a structure in a sample may comprise one or more laser sources configured to generate at least one excitation beam configured to generate pressure in the sample at an excitation location, wherein the one or more laser sources also are configured to generate at least one interrogation beam incident on the sample at the excitation location, at least one portion of the at least one interrogation beam returning from the sample that is indicative of the generated ultrasonic/pressure signals, and a detector configured to detect at least one light property of the at least one returning portion. The at least one light property may include polarization, phase, amplitude, scattering, auto-fluorescence, and second harmonic generation. The at least one light property may include a plurality of light properties, and the detector may be configured to detect the plurality of light properties simultaneously or separately. The PARS may be configured to image the structure of the sample through a glass window holding the sample. The PARS may comprise a plurality of laser sources configured to generate a plurality of excitation beams simultaneously, a plurality of interrogation beams simultaneously, or at least one excitation beam and at least one interrogation beam simultaneously. The PARS may include an endoscope. Furthermore, the PARS may further include an optical system configured to focus the at least one excitation beam at a first focal point and the at least one interrogation beam at a second focal point, wherein the PARS is configured to scan the optical system while the sample remains stationary.

The above-mentioned PARS examples may be used in one or more of the following applications: imaging histological samples; imaging cell nuclei; imaging proteins; imaging cytochromes; imaging DNA; imaging RNA; imaging lipids; imaging of blood oxygen saturation; imaging of tumor hypoxia; imaging of wound healing, burn diagnostics, or surgery; imaging of microcirculation; blood oxygenation parameter imaging; estimating blood flow in vessels flowing into and out of a region of tissue; imaging of molecularly-specific targets; imaging angiogenesis for pre-clinical tumor models; clinical imaging of micro- and macro-circulation and pigmented cells; imaging of the eye; augmenting or replacing fluorescein angiography; imaging dermatological lesions; imaging melanoma; imaging basal cell carcinoma; imaging hemangioma; imaging psoriasis; imaging eczema; imaging dermatitis; imaging Mohs surgery; imaging to verify tumor margin resections; imaging peripheral vascular disease; imaging diabetic and/or pressure ulcers; burn imaging; plastic surgery; microsurgery; imaging of circulating tumor cells; imaging melanoma cells; imaging lymph node angiogenesis; imaging response to photodynamic therapies; imaging response to photodynamic therapies having vascular ablative mechanisms; imaging response to chemotherapeutics; imaging response to anti-angiogenic drugs; imaging response to radiotherapy; estimating oxygen saturation using multi-wavelength photoacoustic excitation; estimating venous oxygen saturation where pulse oximetry cannot be used; estimating cerebrovenous oxygen saturation and/or central venous oxygen saturation; estimating oxygen flux and/or oxygen consumption; imaging vascular beds and depth of invasion in Barrett's esophagus and/or colorectal cancers; functional imaging during brain surgery; assessment of internal bleeding and/or cauterization verification; imaging perfusion sufficiency of organs and/or organ transplants; imaging angiogenesis around islet transplants; imaging of skin-grafts; imaging of tissue scaffolds and/or biomaterials to evaluate vascularization and/or immune rejection; imaging to aid microsurgery; guidance to avoid cutting blood vessels and/or nerves; imaging of contrast agents in clinical or pre-clinical applications; identification of sentinel lymph nodes; non- or minimally-invasive identification of tumors in lymph nodes; imaging of genetically-encoded reporters, wherein the genetically-encoded reporters include tyrosinase, chromoproteins, and/or fluorescent proteins for pre-clinical or clinical molecular imaging applications; imaging actively or passively targeted optically absorbing nanoparticles for molecular imaging; imaging of blood clots; or staging an age of blood clots.

The various embodiments described above are not limited to a particular photoacoustic remote sensing (PARS) system. Rather, they may be applied to the various PARS systems described herein and in U.S. Pat. No. 10,117,583 B2, U.S. Pat. No. 10,327,646 B2, U.S. Patent Publication No. 2019/0104944 A1, U.S. Patent Publication No. 2019/0320908 A1, U.S. Patent Publication No. 2018/0275046 A1, and International PCT Publication No. WO2019/145764, all of which are incorporated by reference herein in their entireties.

Other aspects will be apparent from the description and claims below.

BRIEF DESCRIPTION OF THE DRAWINGS

These and other features will become more apparent from the following description in which reference is made to the appended drawings, the drawings are for the purpose of illustration only and are not intended to be in any way limiting, wherein:

FIG. 4 is a block diagram of a PARS, according to another embodiment.

FIGS. 5A-5I are representative drawings of different overlaps between the excitation and interrogation beams on a sample.

DESCRIPTION

Figure 1A:
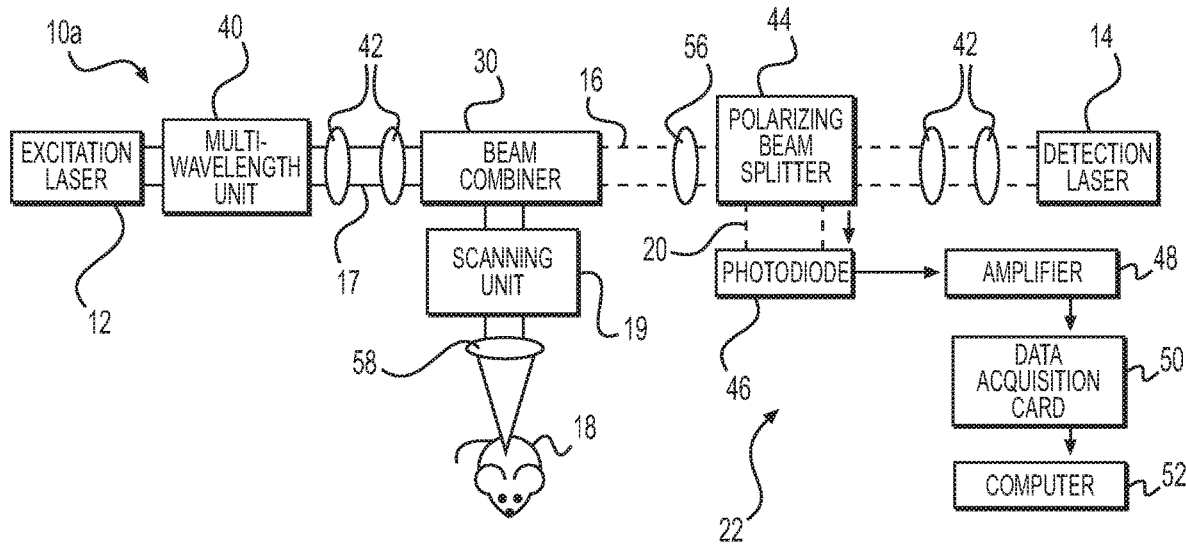
FIGS. 1A-1C are block diagrams of a photoacoustic remote sensing (PARS) microscopy system, according to various embodiments.

Reference will now be made in detail to examples of the present disclosure, which are illustrated in the accompanying drawings. Wherever possible, the same reference numbers will be used throughout the drawings to refer to the same or like parts. In the discussion that follows, relative terms such as "about," "substantially," "approximately," etc. are used to indicate a possible variation of ±10% in a stated numeric value.

Photoacoustic imaging is a biomedical imaging modality that uses laser light to excite tissues. Energy absorbed by chromophores, or any other absorber, is converted to acoustic waves due to thermo-elastic expansion. These acoustic signals are detected and reconstructed to form images with optical absorption contrast. Photoacoustic imaging (PA) has been shown to provide exquisite images of microvessels and is capable of imaging blood oxygen saturation, gene expression, and contrast agents, among other uses. In most PA and ultrasound imaging systems, piezoelectric transducers have been employed, in which an ultrasound coupling medium such as water or ultrasound gel is required. However, for many clinical applications such as wound healing, burn diagnostics, surgery, and many endoscopic procedures, physical contact, coupling, or immersion is undesirable or impractical. The systems described herein are capable of in vivo optical-resolution photoacoustic microscopy using non-contact non-interferometric sensing without use of any ultrasound medium.

The systems described herein, i.e., photoacoustic remote sensing (PARS) microscopy systems, are based on the idea of focusing excitation light to an excitation spot, e.g., an aperture-limited diffraction-limited spot, which is larger than the absolute diffraction-limited spot, and detecting photoacoustic signals using a confocal interrogation beam co-focused with the excitation spot. While previous approaches use a broad excitation beam with powerful lasers delivering mJ-J of pulse energy over a broad area, the PARS microscopy technique described herein uses nJ- or pico joules scale pulse energies focused to excitation spots, e.g., near diffraction-limited spots. It is noted that larger pulse energies may be delivered depending on the size of the excitation spots. Excitation spot sizes, i.e., the diameter of the spots, are not particularly limited. In some examples, excitation spot sizes may be less than 30 µm, less than 20 µm, less than 10 µm, or less than 1 µm. Larger pulse energies may also be appropriate in instances in which the excitation is significantly larger than the diffraction limit. When focusing into tissue, the surface fluence can be maintained below present ANSI limits for laser exposure but the ballistically-focused light beneath the tissue can create fluences transiently far above the ANSI limits (as is done in other microscopy methods). In PARS, this means that very large local fluences ~J/cm2 are created within a micron-scale spot, generating large initial acoustic pressures. For example, at 532-nm excitation wavelength, imaging a capillary with 500 mJ/cm$^2$ local fluence would result in an initial pressure on the order of 100 MPa locally. In the PARS approach, large optically-focused photoacoustic signals are detected as close to the photoacoustic source as possible, which is done optically by co-focusing an interrogation beam with the excitation spot.

Some examples of interferometric PARS systems, e.g., coherence gated photoacoustic remote sensing (CG-PARS) systems, may perform optical depth scanning of samples. CG-PARS and other PARS systems may be optimized in order to take advantage of a multi-focus design for improving the depth-of-focus of 2D and 3D optical resolution (OR) PARS imaging. The chromatic aberration in a collimating and objective lens pair may be harnessed to refocus light from a fiber into the object so that each wavelength is focused at a slightly different depth location. Using these wavelengths simultaneously may be used to improve the depth of field and signal to noise ratio (SNR) of PARS images. During PARS imaging, depth scanning by wavelength tuning may be performed.

Other examples of PARS systems may not perform optical depth scanning. Since depth scanning is not performed with certain embodiments of NI-PARS, NI-PARS can perform in near real time using a high pulse repetition laser and fast scanning mirrors. However, most previous non-contact photoacoustic detection methods have not shown real-time imaging capability and optical resolution was not demonstrated. Embodiments of the disclosure optically focus a pulsed excitation laser into superficial tissues to generate high micro-scale initial pressures. Then, these large optically-focused photoacoustic signals are harvested as close to the photoacoustic source as possible. This is done by detecting photoacoustic signals using a confocal interrogation beam co-focused and co-scanned with the excitation spot. Local initial pressures are very large when optical focusing and thermal confinement conditions are applied. These large initial pressures can cause significant refractive index mismatch regions which are measured by the NI-PARS as changes in reflected light.

Furthermore, PARS is not limited to the application of a singular excitation beam and/or a singular detection/interrogation beam. For example, a PARS may focus a plurality of excitation beams to a spot, e.g., aperture-limited diffraction-limited spot, near diffraction-limited spot, and/or a plurality of interrogation beams at the excitation spot. As discussed above, the size of the excitation spot is not particularly limited, and may be less than 30 µm, less than 20 µm, less than 10 µm, or less than 1 µm. PARS may further include a plurality of detectors configured to detect the returning photoacoustic signals. Such systems may provide additional advantages and benefits, including flexibility and sequential sample interrogation.

Embodiments of the present disclosure are related to an ultrasound/photoacoustic imaging detection mechanism based on pressure-induced refractive-index modulation as well as real-time non-contact detection. This approach contemplates interrogating subsurface absorption with optical resolution using a non-contact system. The range of subsurface depth is not particularly limited, and in some examples, may range from about 50 nm to 8 mm. Thus, subsurface absorption depths in some examples may be very small such as in, e.g., skin samples, or histology glass slides. In some instances, some portion (e.g., half) of the excitation spot may be inside the sample while another portion (e.g., the other half) may be outside of the sample.

The high sensitivity and the fine resolution of the proposed system offer performance comparable to other in vivo optical resolution photoacoustic microscopy systems, but in a non-contact reflection mode suitable for many clinical and pre-clinical applications.

Various embodiments of photoacoustic remote sensing microscopy systems (PARS) are depicted through FIGS. 1A-4. Variations to the depicted systems will be apparent to those skilled in the art.

Referring to FIG. 1A, a block diagram of an embodiment of a PARS 10*a*. A multi-wavelength fiber excitation laser 12 is used in multi focus form to generate photoacoustic signals. Excitation laser 12 may operate in the visible, ultraviolet or near-infrared spectrum, although the particular wavelength may be selected according to the requirements of the particular application. An excitation beam 17 passes through a multi-wavelength unit 40, and both excitation beam 17 and an interrogation beam 16 pass through a lens system 42 to adjust their focus on a sample 18. Excitation beam 17 and interrogation beam 16, the paths of which are diametrically across from one another, will be combined using a beam combiner 30. The acoustic signatures are interrogated using either a short or long-coherence length probe beam 16 from a detection laser 14 that is co-focused and co-aligned with the excitation spots on sample 18. Interrogation/probe beam 16 passes through a polarizing beam splitter 44 and quarter wave plate 56 to guide the reflected light 20 from sample 18 to the photodiode 46. However, PARS 10*a* is not limited to including polarizing beam splitter 44 and quarter wave plate 56. The aforementioned components may be substituted for fiber-based, equivalent components, e.g., a circulator, coupler, WDM, and/or double-clad fiber, that are non-reciprocal elements. Such elements may receive light from a first path, but then redirect said light to a second path. A combined beam 21 of excitation beam 17 and interrogation beam 16 will be scanned by scanning unit 19. The scanned combined beam 21 will pass through an objective lens 58 and focus on the sample 18. The reflected beam 20 returns along the same path and is analyzed by detection unit 22. Unit 22 includes amplifier 48, fast data acquisition card 50 and computer 52.

Figure 1B:
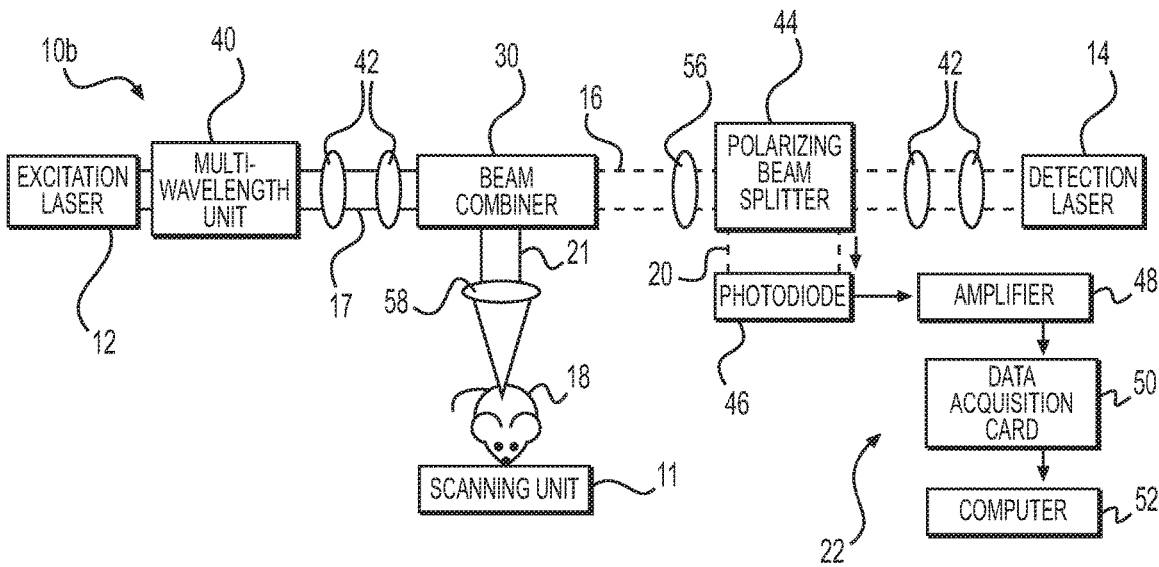

FIG. 1B shows another embodiment of a PARS 10*b*, in which scanning unit 19 (shown in FIG. 1A) is replaced by scanning unit 11 in order to scan (move) the sample 18 in relation to the fixed combined beams 21. In some other embodiments, PARS systems may include both scanning unit 11 and scanning unit 19, thereby having scanning units on opposite ends of combined beam 21.

Figure 1C:
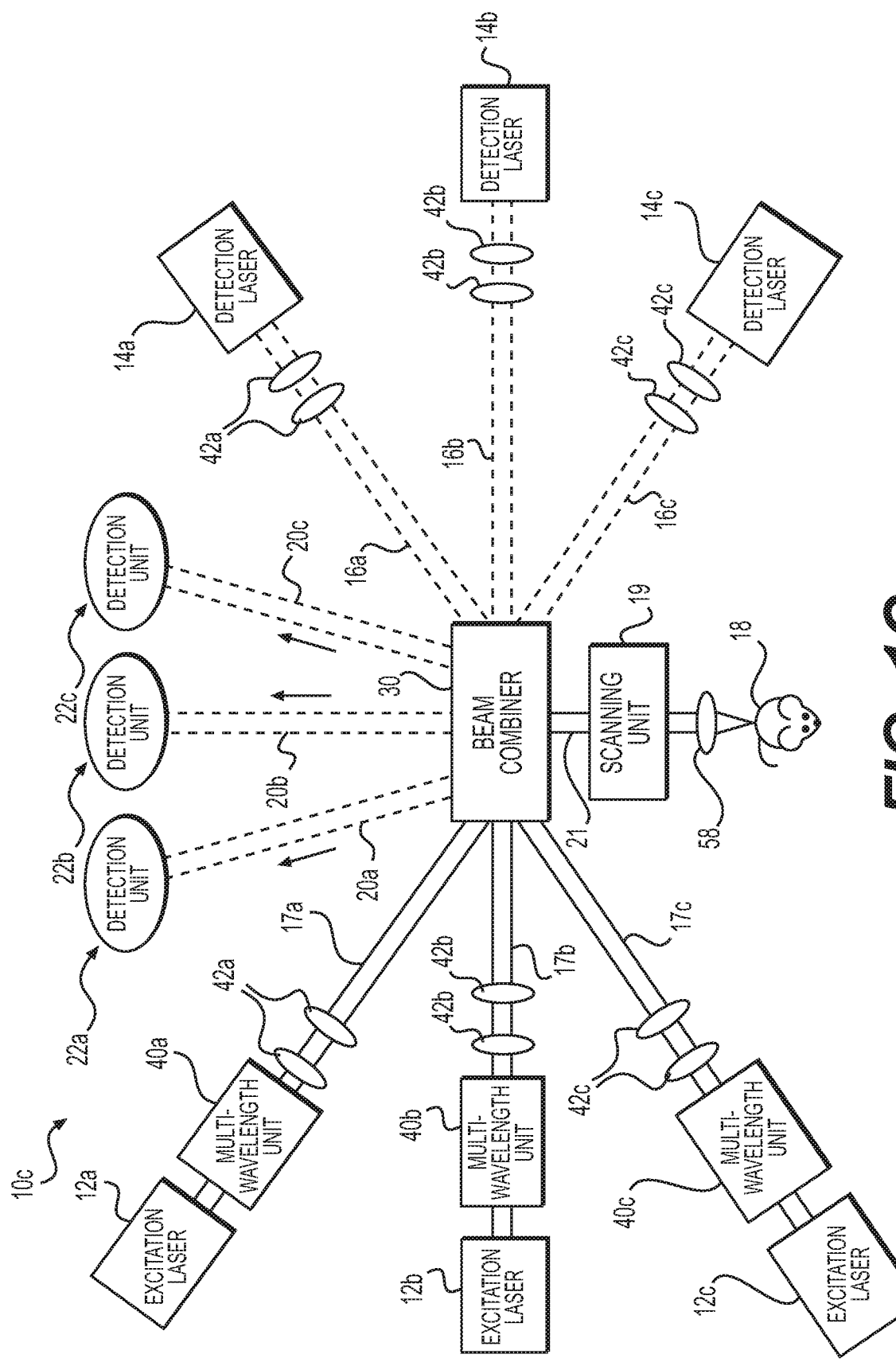

FIG. 1C is another block diagram of an embodiment of a PARS 10*c*. PARS 10*c* includes three excitation lasers 12*a*-12*c* configured to provide three excitation beams 17*a*-17*c*, three detection lasers 14*a*-14*c* configured to provide three interrogation beams 16*a*-16*c*, and three detection units 22*a*-22*c* to receive and analyze reflected beams 20*a*-20*c*. It is noted, however, that the number of excitation lasers, detection lasers, and detectors is not particularly limited, and any suitable number of lasers and configurations thereof may be used, such as, for example, two, four, five, or more. Similar to PARS 10*a*, excitation beams 17*a*-17*c* and interrogation beams 16*a*-16*c* combine via beam combiner 30 to focus combined beam 21, passing through objective lens 58, onto sample 18. Reflected beams 20a-20c reflect in directions opposite of combined beam 21, and are received by detection units 22a-22c. Beam combiner 30 may serve additional functions in PARS 10c, including serving as a polarizing beam splitter of interrogation beams 16a-16c and as a guide for re-directing reflected beams 20a-20c toward detection units 22a-22c. Detection units 22a-22c may respectively include an amplifier (not shown), a fast data acquisition card (not shown), and a computer (not shown), such as amplifier 48, fast data acquisition card 50, and computer 52 set forth above with respect to FIG. 1A.

PARS 10c, including a plurality of excitation beams and/or interrogation beams and or detectors, may provide users with the option of applying beams of varying properties, e.g., wavelength, for various aims. For example, to image deep-inside biological tissues, it may be desirable to use a deeply-penetrating (long transport mean-free-path) optical wavelength such as a short-wave infrared wavelength. An example of a deeply-penetrating wavelength is 1310 nm, which is typically used in PARS for deep imaging. Alternatively, when imaging superficial targets, there may be geometric benefits (in terms of a smaller focal spot size) and sensitivity benefits (in terms of increased scattering) to using a shorter, visible wavelength, such as 630 nm. The combination of such geometric and sensitivity benefits can result in several orders of magnitude difference in the amount of returned light from an imaged sample. For instance, the focal spot area for 500 nm light will be roughly 9 times smaller than that of 1500 nm light for the same focusing optics. Likewise, for biological tissues, the scattering at 500 nm can be 3 to 4 times stronger than at 1500 nm, for example. Thus, such benefits from using a wavelength of 500 nm, as opposed to a wavelength of 1500 nm, may ultimately result in a 30 to 40-fold detection sensitivity improvement at superficial depths. It is noted that excitation wavelengths are not particularly limited to the aforementioned example values, and may be any wavelengths suitable for the intended purpose. The two properties of deep sample penetration and improved superficial performance may also be desirable for use at the same time, or as a switchable option depending on the desired outcome of an imaging session. For example, both beams may be used at the same time if imaging near-surface capillary vessels followed by deeper vessels with a single volumetric scan. The superficial structures may benefit from the improved resolution and sensitivity of the shorter detection wavelength, whereas the deeper structures may only be recovered by using the infrared wavelengths. However, the use of two beams at the same time may provide too much exposure to optical radiation, and thus a switching approach may be taken where the shorter detection wavelength is traded for the longer wavelength detection at an appropriate depth in the sample. Thus, PARS having a plurality of excitation beams and/or interrogation beams and/or detectors may allow a user to implement two or more detections in the same system, thereby allowing the user to examine the effectiveness of each detection on a sample. Some samples may provide specific improved contrast for a given detection wavelength over others, due to the nature of light scattering and extinction at particular wavelengths. Multiple detection paths may also be combined using free-space optical beam combiners such as a dichroic or beam-splitters or using fiber-based devices such as couplers or wavelength division multiplexers.

A plurality of excitation wavelengths may also be used sequentially while acquiring multiplexed/functional information from a single sample, such as imaging oxy- and deoxyhemoglobin for visualization of blood oxygenation, or targeting DNA and cytochrome absorption peak to extract histological information from a tissue sample. To facilitate rapid and consistent imaging, which may minimize the potential for motion artifacts and may allow for video-rate real-time multiplexed/functional imaging, the plurality of excitation wavelengths may be used in close succession to one another, for example, up to MHz-range repetition rates, so that the plurality of excitation beam sources are set-up and active simultaneously in the same –PARS. Multiplexed/functional information may also be extracted from a sample using variations in pulse-widths. These widths are not particularly limited, and may vary from the thermal and stress confinement conditions in the hundreds of nanoseconds, or down to the femtosecond range. For example, oxygenated and deoxygenated hemoglobin can be separated using two 532 nm sources, one which provides picosecond-scale pulse widths and the other operating in the nanosecond regime (provides nanosecond-scale pulse widths). In general, PARS excitation paths may include any combination of wavelengths, pulse widths, repetition rates, and pulse energies, which provide various benefits in terms of sample exposure, imaging sensitivity, imaging specificity, and chromophore de-mixing. The multiple excitation beam paths may be combined using free-space optical beam combiners such as a dichroic or beam-splitters or using fiber-based devices such as couplers or wavelength division multiplexers.

Thus, a PARS including a combination of multiple detection/interrogation beams and excitation beams may provide highly tunable imaging parameters. As discussed above, such a system may be configured to image deeply in scattering tissue to target near-infrared blood absorption. The same system may be configured to use a short-wave infrared detection providing penetration depths approaching 3 mm for optical resolutions that are less than 2 µm, and beyond this depth with decreased resolving powers. This may be done sequentially or simultaneously within the same PARS. The same system may also use a UVC excitation, having wavelengths of 200 to 280 nm, to target DNA absorption, and use UVA detection, having wavelengths of 315 to 400 nm, to provide superficial imaging performance with resolutions on the order of several hundred nanometers. UVB beams also may be utilized for excitation/detection.

Figure 2A:
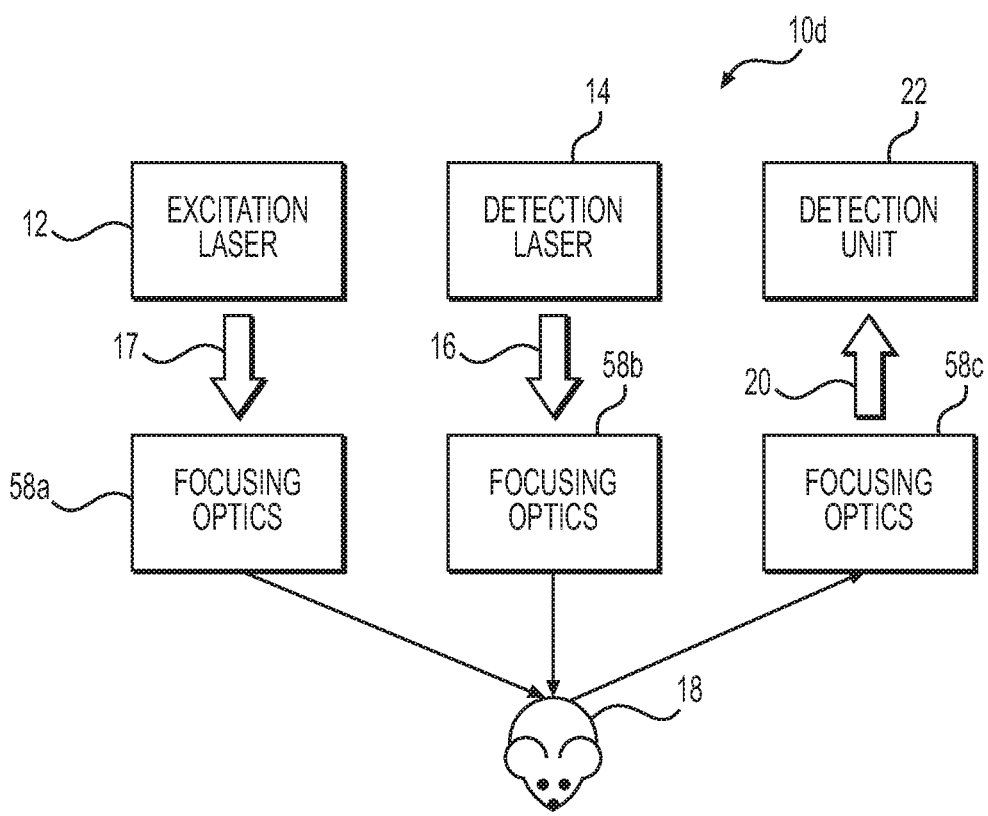
FIG. 2A is a block diagram of a PARS, according to other embodiments.

FIG. 2A shows an embodiment of PARS 10d, which includes individual optical systems, adjacent to one another, which are separately configured to focus excitation beam 16, interrogation beam 17, and receive reflected beam 20, respectively. In PARS 10d, excitation beam 16 and interrogation beam 17 are not combined via a beam combiner, and co-focus on sample 18, via separate focusing optics, i.e., 58a and 58b. Focusing optics 58a and 58b may include any device(s) used to converge the beam of light, such as an objective lens or curved mirror. It is noted that the central axes of excitation beam 16 and interrogation beam 17 are angled and offset relative to each other, but that the angle is not particularly limited. Reflected beam 20 returns along a different path that is angled and offset to the axis of interrogation beam 16, and reflects back towards focusing optics 58c, which guides reflected beam 20 to detection unit 22.

Figure 2B:
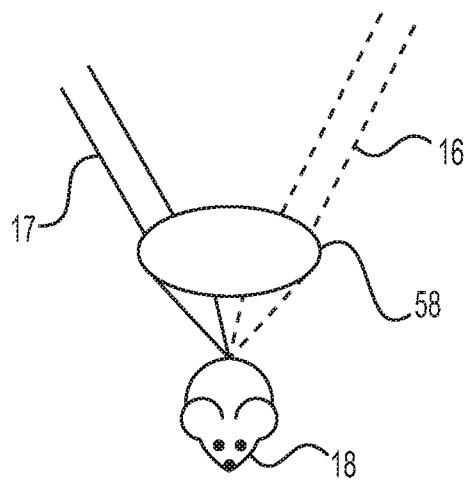
FIGS. 2B and 2C are illustrations of excitation and detection beams on a sample.
Figure 2C:
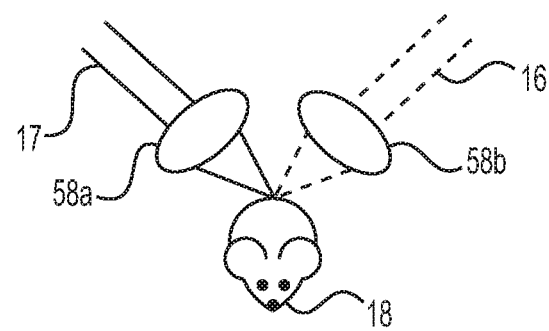
Figure 2D:
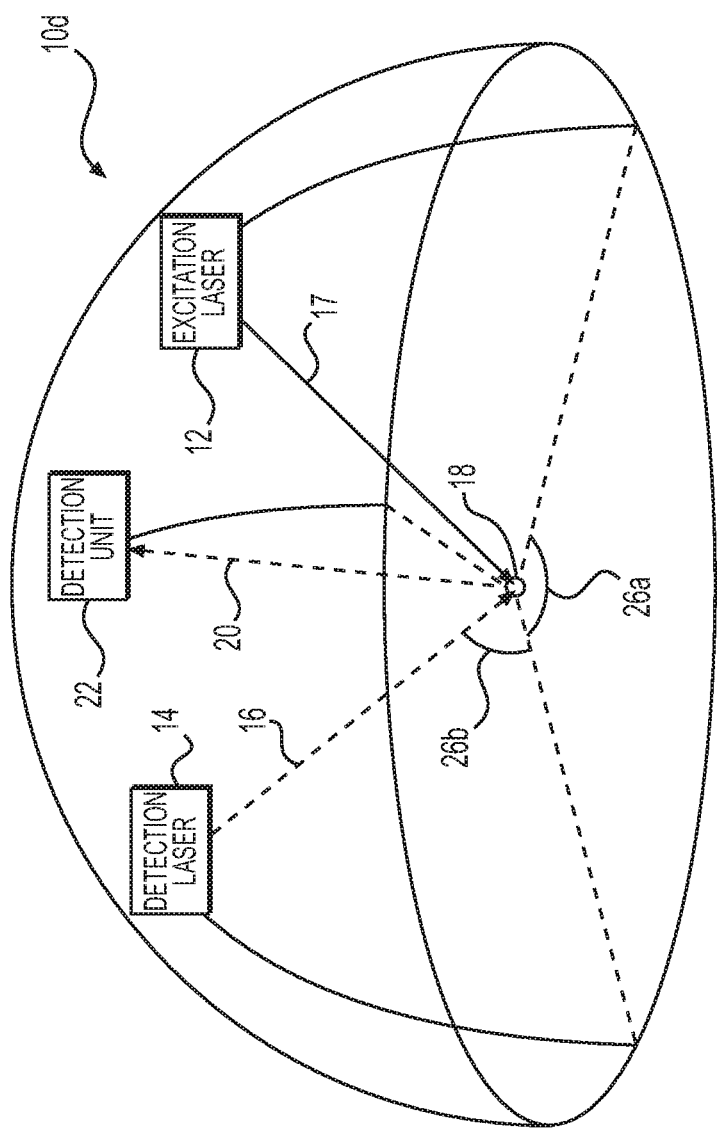
FIG. 2D is a three-dimensional illustration showing excitation and detection beams applied to a sample, along with a returning portion of the detection beam.

Similar to PARS 10d, FIGS. 2B and 2C further show excitation beam 17 and interrogation beam 16 being directed to sample 18 at an angle relative to one another. However, unlike system 10d, FIGS. 2B-2C illustrate the use of refractive optics, as opposed to reflective optics, such as, e.g., mirrors. In FIG. 2B, both excitation beam 17 and interrogation beam 16 pass through a single objective lens 58, which co-focuses beams 16 and 17 on sample 18 from two distinct angles. While the refracted portions of beam 16 and 17 are off their respective longitudinal axes (of beams 16 and 17 prior to passing through lens 58), the refracted beams are still parallel to said axes such that beams 16 and 17 are able to co-focus onto the same spot of sample 18. Because there is a single objective lens 58 in FIG. 2B, the angle between beams 16 and 17 may be relatively shallow in comparison to systems in which two lenses may be used. However, the use of single objective lens 58 may also allow for relatively easier co-alignment of beams 16 and 17 onto sample 18.

In contrast, in FIG. 2C, excitation beam 16 and interrogation beam 17 each pass through their respective objective lens, i.e., objective lens 58b and objective lens 58a. Moreover, beams 16 and 17 remain centered along their respective longitudinal axes to co-focus onto the same spot of sample 18. Because there are separate objective lenses 58b and 58a for beams 16 and 17, respectively, the range of the angle between beams 16 and 17 may be more flexible and larger angles than the embodiment shown in FIG. 2B. Such a configuration may also enable higher levels of polarization. However, the embodiment shown in FIG. 2C requires co-alignment of objective lenses 58b and 58a so that beams 16 and 17 may co-focus onto sample 18. Other PARS embodiments, may also include additional individual optical systems, and/or may be in different configurations or arrangements relative to one another.

The configuration of PARS 10d, and the beam configurations shown in FIGS. 2A-2C may provide added spatial rejection of undesired randomly scattered photons, and detect only photons that have been modulated by excitation laser 12. Since the PARS imaging region is defined by the overlap of excitation beam 16, detection/interrogation beam 17, and backwards detection/reflected beam path 20, if these paths are all co-aligned, the interrogated region on sample 18 may be defined by a radial distribution which is commonly shorter than the axial distribution. This may cause the axial resolution of such imaging systems to be larger, and thus, worse than the lateral resolution. By angling excitation beam 16 and interrogation beam 17 relative to each other, as shown in PARS 10d and the beams shown in FIGS. 2A-2C, the overlap may now be defined between the combination of two or three radial distributions. This allows for the lateral resolution of one of the beams to improve upon the axial performance provided by the other beam. To maximize this effect, it may be most advantageous to have the three beams evenly distributed in the azimuth and with around 45 degrees each to the sample surface. This is shown in FIG. 2C, which illustrates sample 18 on a plane, and excitation beam 17, interrogation beam 16, and reflected interrogation beam 20 having beam paths, originating from sample 18, of congruent azimuth angles 26a, i.e., 120°. The beam paths also have congruent altitude angles 26b, which may range from 20-90°. However, in other embodiments the altitude angles may vary amongst the beam paths. Decreasing internal angles between beams 16, 17, and 20 may simply begin to approach the performance of non-angled PARS for decreasing internal angles, and become unpractical as angles approach 180 degrees since samples are generally flat.

As shown in FIGS. 2A-2C, the angling of the focused paths of excitation beam 16 and interrogation beam 17 may be achieved through angling of the input beams into a single focusing element, i.e., objective lens 58 shown in FIG. 2B, or by constructing a system with multiple focusing elements which are angled to each other, i.e., objective lens 58 and 15 shown in FIG. 2C, or some combination of the two. As a result, the axes of excitation beam 16 and interrogation beam 17 may be angled relative to one another.

PARS including an excitation source, a detection source, a beam combiner combining excitation beam(s) and interrogation beam(s), focusing optics, and a detector, similar to the embodiment in FIG. 1A, capture intensity modulations in the collected light/reflected beam from the sample. This may be done by sensing the change in scattering from the sample. Other non-PARS or devices that may perform such a function include scattering microscopes, which may include a detection beam from a detection source passing through a combiner/splitter to focusing optics, which focus the beam onto a sample, and an intensity detector configured to receive reflected interrogation/detection beams (with no excitation beam).

However, the reflected interrogation beam also contains information regarding its polarization state and its phase, and there are conventional, non-PARS or devices that may capture polarization and phase accumulation. One such device may be a polarization-based microscope, which is similar to the above described scattering microscope, except a polarization detector is used in place of an intensity detector. Another such device may be a conventional phase microscope, which may include a detection beam from a detection source passing through an interferometer to focusing optics, which focus the beam onto a sample, and a phase detector configured to receive reflected interrogation/detection beams that return through the interferometer. Thus, PARS of the present disclosure modulate the scattering properties of reflected beam 20 and also respectively modulate the apparent polarization and phase accumulation within a sample. Such PARS are further discussed below, referring to FIGS. 3A and 3B.

Figure 3A:
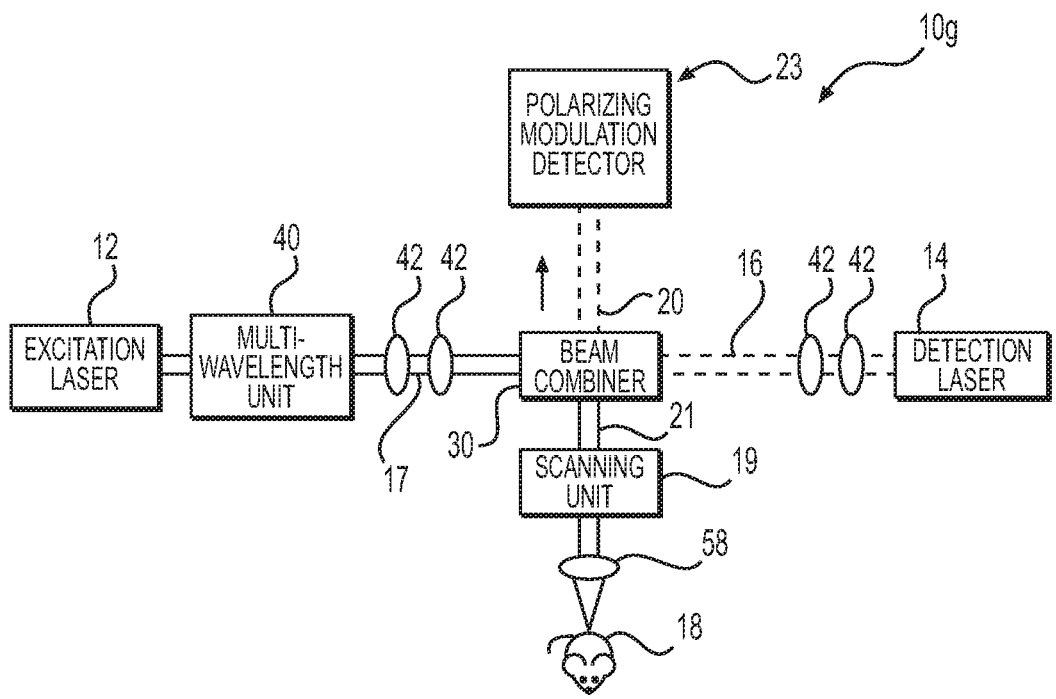
FIGS. 3A-3B are block diagrams of a PARS, according to other embodiments.

FIG. 3A shows another block diagram of an embodiment of PARS 10g. PARS 10f includes excitation laser 12 configured to provide excitation beam 17, and detection laser 14 configured to provide interrogation beam 16. However, as previously discussed, the number of excitation lasers and detection lasers is not particularly limited, and any suitable number of lasers and configurations thereof may be used. Similar to PARS 10a, excitation beam 17 and interrogation beam 16 combine via beam combiner 30 to focus combined beam 21, passing through objective lens 58, onto sample 18. Furthermore, in this embodiment, beam combiner 30 may also serve the function of a polarizing beam splitter of interrogation beam 16. However, PARS 10f does not include the detection unit 22 shown in FIG. 1A. Instead, reflected beam 20 is reflected back through beam combiner 30, which guides reflected beam 20 to a polarization modulation detector 23. It is noted that a quarter waveplate is not used in PARS 10g, so that the polarization state of reflected beam 20 may be maintained when guided toward polarization modulation detector 23.

More specifically, to capture polarization modulation, interrogation beam 16 with a controlled polarization is fed into sample 18, where reflected light 20 is now separated based on its polarization content. The means by which polarization is controlled in not particularly limited, and can be, e.g., a conventional polarization controller, and in some embodiments, beam 16 may already be polarized when emitted from laser 14. For example, vertically polarized light may be directed to one photodetector within detector 23 and horizontally polarized light may be directed to another photodetector within detector 23. Different aspects of polarization could be used such as linear direction, handedness of circular polarized states, and higher-dimensional polarization distributions, such as radially and azimuthally polarized states. Separation and characterization of these states may be accomplished with polarization sensitive detectors, i.e., polarization modulation detector 23, quarter wave plate 56, and polarization-sensitive splitters (not shown). This may allow for precise characterization of the polarization shift, as the modulated value could be directly compared with the un-modulated value at the same sample location.

Figure 3B:
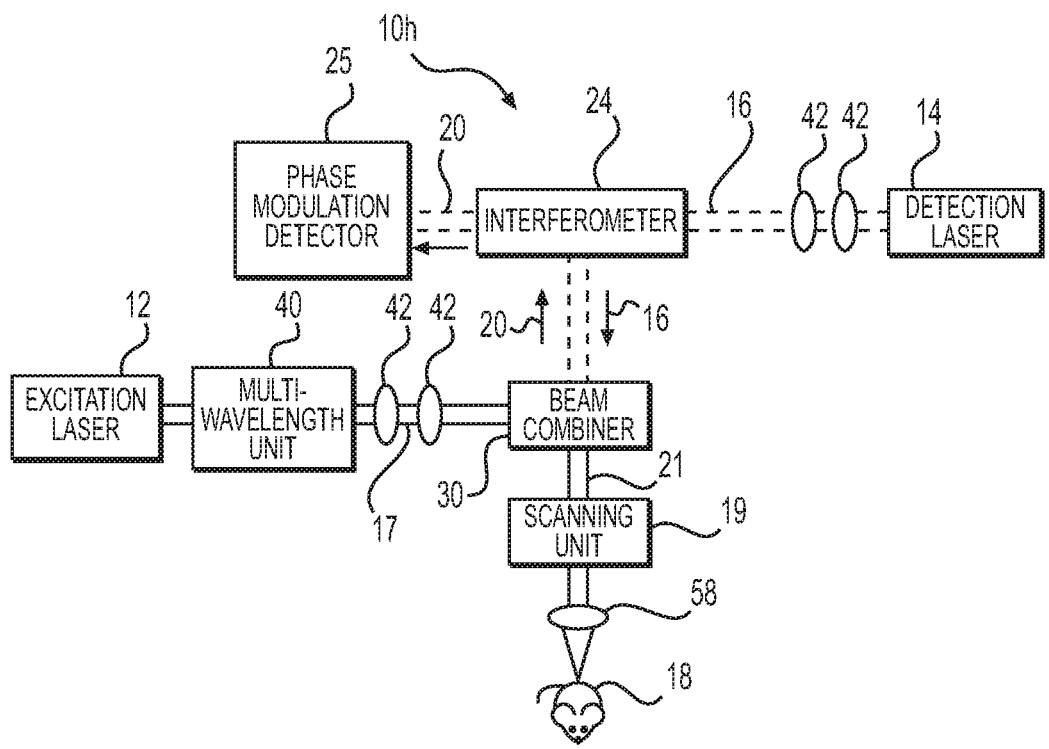

FIG. 3B shows an embodiment of PARS 10h also including excitation laser 12 configured to provide excitation beam 17, and detection laser 14 configured to provide interrogation beam 16. PARS 10g includes an interferometer 24 and a phase modulation detector 25. PARS 10g may be arranged so that interrogation beam 17 passes through interferometer 24 and is guided to beam combiner 30, at which interrogation beam 17 combines with excitation beam 16. Reflected beam 20 from sample 18 returns along the same path of interrogation beam 17 up until interferometer 24, at which reflected beam 20 is then guided towards and received by phase modulation detector 25.

To capture phase shifting, a phase sensitive detector, i.e., phase modulation detector 25, is implemented. This may be done with heterodyne and homodyne interferometry, which may capture a component of or the full quadrature of returning light 20 from sample 18. This would allow for precise characterization of the phase shift, as the modulated value could be directly compared with the un-modulated value at the same sample location.

Any combination of these six light properties (e.g., scattering, polarization, phase, and their respective modulations) may be captured and analyzed in a PARS via any suitable mechanism, e.g., phase modulation detector 25 for phase, where the contrast mechanisms may provide unique and complementary information. For example, PARS may generate strong second harmonic signals, and auto-fluorescence from the sample due to the PARS effect. For example, there may be poor scattering contrast, but strong polarization contrast from sample 18. While conventional imaging systems may not be configured to find such a signal, polarization-sensitive detection via polarization modulation detector 23 may provide improved results. By using the additional information contained within the polarization and phase of reflected beam 20, added sensitivity may be achieved by averaging across shifts, resulting in lower required optical exposure. Complementary information may be found between these shifts which give optical absorption information, and the unshifted values may yield scattering, polarization, and phase in their own right. Such wealth of information may be used to drastically improve specificity, since given targets will provide unique signatures across these six modalities (e.g., conventional scattering microscope, conventional polarization-based microscope, conventional phase microscope, a PARS microscope, and the microscopes shown in FIGS. 3A and 3B), allowing for improved multiplexing capabilities.

FIG. 4 shows another embodiment of PARS 10i, in which excitation beam 17 and interrogation beam 16 have separated paths, and are not combined. In this embodiment, interrogation beam 16 is focused, using another objective lens 15, to sample 18. In other embodiments, PARS 10i may be similar to aspects of both PARS 10c and 10d, shown in FIGS. 1C and 2A. Similar to PARS 10c, PARS 10i may have multiple excitation lasers, detection lasers, and detection units, the number of which are not particularly limited.

In some embodiments, both beams may be scanned together. Alternatively, one beam may be fixed while the other beam may be scanned. In other embodiments, sample 18 may be scanned while both beams are fixed. Sample 18 may also be scanned while both beams are scanning. Sample 18 may also be scanned while one beam is fixed and the other is scanning.

It will be apparent to one of ordinary skill in the art that other PARS embodiments may be designed with different components to achieve similar results. For example, other embodiments may include all-fiber architectures where circulators replace beam-splitters similar to optical-coherence tomography architectures. Other alternatives may include various coherence length sources, use of balanced photodetectors, interrogation-beam modulation, incorporation of optical amplifiers in the return signal path, etc.

The PARS takes advantage of two focused laser beams on the sample which may simulate a confocal PAM configuration.

PARS also takes advantage of optical excitation and detection which may help dramatically reduce the footprint of the system. The absence of a bulky ultrasound transducer makes this system suitable for integrating with other optical imaging systems. Unlike many previous non-contact photoacoustic imaging systems, the PARS is capable of in vivo imaging. It relies on a much simpler setup and takes advantage of recording the large initial ultrasound pressures without appreciable acoustic losses.

During in vivo imaging experiments, no agent or ultrasound coupling medium are required. However, the target may be prepared with water or any liquid such as oil before a non-contact imaging session. PARS does not require a floating table unlike many other interferometric sensors. No special holder or immobilization is required to hold the target during imaging sessions. However, a cover slip may be implemented to flatten the target. In some instances, glass windows for the targets, e.g., resected tissue, to sit on may be necessary, and imaging may be performed through said glass windows. This may help image flat surfaces of the target.

Other advantages that are inherent to the structure will be apparent to those skilled in the art. The embodiments described herein are illustrative and not intended to limit the scope of the claims, which are to be interpreted in light of the specification as a whole.

In PARS, a pulse laser is used to generate photoacoustic signals and the acoustic signatures are interrogated using either a long-coherence or short-coherence length probe beam co-focused with the excitation spots. The PARS may be utilized to remotely record the large local initial pressures from chromophores and without appreciable acoustic losses due to diffraction, propagation and attenuation.

The excitation beam may be any pulsed or modulated source of electromagnetic radiation including lasers or other optical sources. In one example, a nanosecond-pulsed laser may be used. The excitation beam may be set to any wavelength suitable for taking advantage of optical (or other electromagnetic) absorption of the sample. The source may be monochromatic or polychromatic.

The interrogation beam may be any pulsed, continuous, or modulated source of electromagnetic radiation including lasers or other optical sources. Any wavelength may be used for interrogation purpose depending on the application.

The chromatic aberration in the collimating and objective lens pair may be harnessed to refocus light from a fiber into the object so that each wavelength is focused at a slightly different depth location. Using these wavelengths simultaneously may improve the depth of field and SNR for structural imaging of microvasculature with OR-PAM.

Since a NI-PARS is not interferometric, the probe/receiver/interrogation beam of NI-PARS, may be a long-coherence or a short-coherence length probe beam, without need of any reference beam or reference arm. Using a short-coherence length, however, may ensure preclusion of interference from reflections in the system or sample to avoid unwanted signals and to extract only photoacoustic initial pressures.

Unlike optical coherence tomography (OCT) or interferometry detection of photoacoustic signal, the NI-PARS detects the changes in the amount of the reflected light from sample due to acoustic pressure and no interferometry design such as, reference beam, reference arm or axial scanning of reference beam are needed.

Various PARS systems (including, but not limited to PARS, NI-PARS, CG-PARS, C-PARS, and SS-PARS) may be integrated with OCT to provide a complete set of information offered by both photoacoustic and OCT systems.

Furthermore, the various PARS with short or long-coherence beams may be used for either optical resolution photoacoustic microscopy (OR-PAM) or common photoacoustic microscopy (PAM), or may be combined with 2nd or 3rd harmonic, fluorescent, multiphoton, Raman, and/or other, microscopes.

In one example, both excitation and receiver beam may be combined and scanned. In this way, photoacoustic excitations may be sensed in the same area as they are generated and where they are the largest. Other arrangements may also be used, including, keeping the receiver beam fixed while scanning the excitation beam or vice versa, and scanning the optics mechanically while the sample remains stationary, such as, for example, in a surgical microscope where the patient must remain stationary. Galvanometers, MEMS mirrors and stepper/DC motors may be used as a means of scanning the excitation beam, probe/receiver beam or both.

The configurations shown in FIGS. 5A-5D may be used to perform PARS and NI-PARS imaging. In the depicted embodiments, excitation beams 502 are depicted with a larger radius of curvature, and receiver/detection beams 504 are depicted with a smaller radius of curvature. FIG. 5A shows an embodiment of a confocal photoacoustic system where excitation beam 502 and probing receive beam 504 are focused on the same spot, which can be on a micron- or sub-micron scale. In FIG. 5B, the optical resolution may be provided by receiver beam 504, rather than excitation beam 502. FIG. 5C shows excitation beam 502 and receiver beam 504 focused on different spots, and takes advantage of ultrasound time of flight in order to locate excitation beams 502 and receiver beams 504 at different positions. In FIG. 5D, optical resolution may be provided by excitation beam 502. Preferably, the focus of either or both of excitation beam 502 and detection beam 504 is less than 30 µm, less than 10 µm, less than 1 µm, or to the diffraction limit of light. A tighter focus may result in a higher possible resolution and a better signal to noise ratio in the reflected beam that is detected. As used herein, the term "focus" is intended to refer to the focal zone of the beam, or the point at which the beam spot size is at the tightest size, and where the diameter of the focal zone is 30% greater than the diameter of the beam spot size. Also preferably, the excitation and detection beams 502 and 504 are focused on the same position, although there may be some spacing between the respective focuses as shown in FIG. 5C. In FIG. 5C, the beams may be focused at different locations, but preferably within 1 mm, 0.5 mm, 100 µm or within the range of the largest focus of the beam. In FIGS. 5A, 5B, and 5D, the beams may be confocal, or may overlap within the focus of the beam with the largest focus. For example, in FIG. 5A, excitation beam 502 is larger than detection beam 504, and detection beam 504 is directed at a location within the focus of excitation beam 502. By moving detection beam 504, the area within excitation beam 502 may be imaged. By having confocal beams, both beams may be moved to image the sample.

One or both of the beams are preferably focused below the surface of the sample. Generally speaking, the beams may be effectively focused up to 8 mm (or more) below the surface of the sample. The beams may be focused at least 50 nm (or even less) below the surface, or focused such that focal point of the beam is at least the distance of focal zone of the beam below the surface of the sample. It will be understood that, while both beams are preferably focused below the surface, in some embodiments either the excitation beam or the interrogation beam may be focused below the surface, with the other focused on, for example, the surface of the sample. In cases where only one beam is focused below the surface of the sample, the separation between the beams discussed previously will be a lateral separation, i.e. in the plane of the sample and orthogonal to the depth of the sample.

Figure 5E:
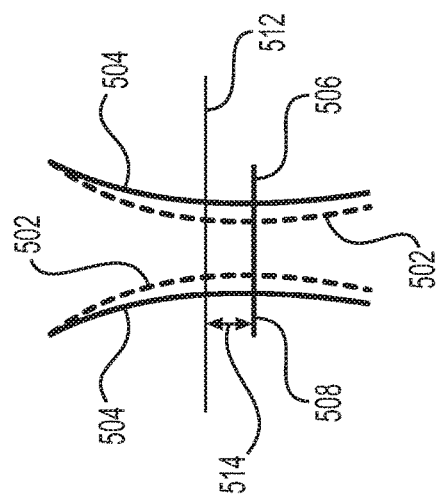
Figure 5F:
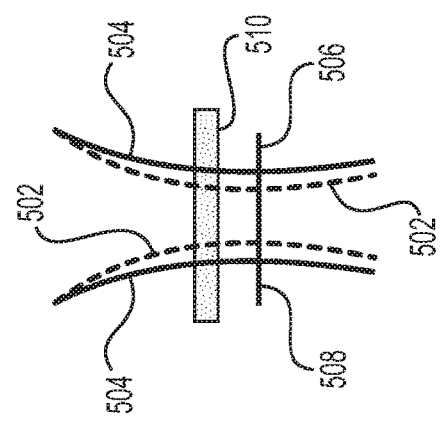
Figure 5H:
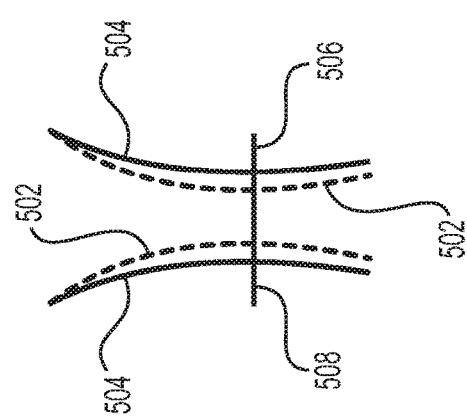
Figure 5G:
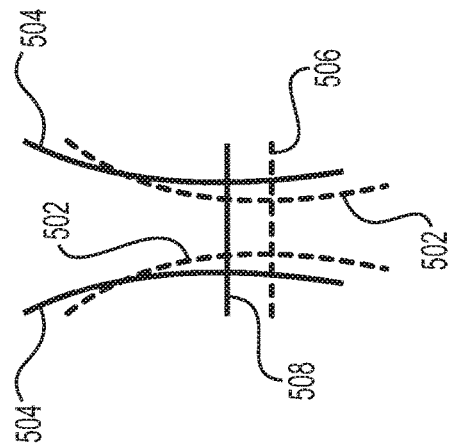
Figure 5I:
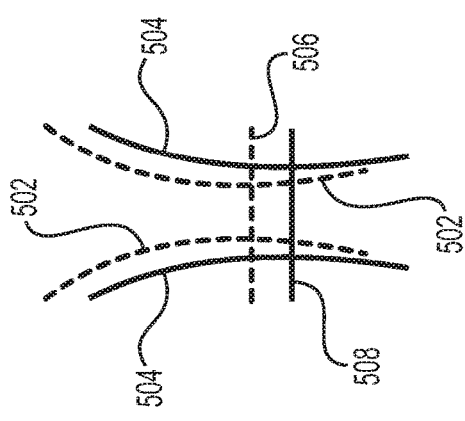

The relationship between excitation beams and detection beams, specifically, their focal planes, subsurface of a sample is further illustrated in FIGS. 5E-5I. For example, FIG. 5E illustrates a confocal photoacoustic system including excitation beam 502 and detection beam 504, where an excitation focal plane 506 and a detection focal plane 508 are focused at the same depth, thereby exhibiting a co-alignment condition. This is similarly illustrated in FIG. 5F, except FIG. 5F further illustrates that the co-aligned focal planes 506 and 508 are below a glass window 510. Thus, in this instance, co-alignment takes place through window 510. The distance between glass window 510 and focal planes 506 and 508 is not particularly limited. FIG. 5G again illustrates co-alignment between focal planes 506 and 508. However, FIG. 5G shows that focal planes 506 and 508 are subsurface of sample 512, by a depth defined by a distance 514. Thus, FIG. 5G illustrates excitation beam 502 and detection beam 504 co-focusing on a spot below the surface of sample 512. The depth of focal planes 506 and 508 below the surface 512 is not particularly limited, and in some instances, may range from 100 nm to 1 µm. FIG. 5H illustrates an instance in which excitation beam 502 is focused, relative to detection beam 504, so that excitation focal plane 506 is above detection focal plane 508. In contrast, FIG. 5I illustrates an instance when excitation focal plane 506 is below detection focal plane 508. Thus, FIGS. 5H-5I illustrate that focal planes 506 and 508 may be out of alignment. An example of when focal planes 506 and 508 are misaligned may be when a PARS system is aligned for imaging near the surface of a sample, and a user of said PARS system attempts to focus deeper in the sample without any adjustments. This results in chromatic aberrations, which cause the detection and excitation focal planes to shift away from one another. Focal planes 506 and 508 may be misaligned by 10 µm, 20 µm, 30 µm, etc. However, the distance between the focal planes is not particularly limited, and may be any suitable distances. Furthermore, it may be preferable to minimize the distance between focal planes 506 and 508 for optimal sensitivity.

The excitation beam and detection/receiver beam may be combined using dichroic mirrors, prisms, beamsplitters, polarizing beamsplitters etc. They may also be focused using different optical paths.

The reflected light may be collected by photodiodes, avalanche photodiodes, phototubes, photomultipliers, CMOS cameras, CCD cameras (including EM-CCD, intensified-CCDs, back-thinned and cooled CCDs), spectrometers, etc. The detected light may be amplified by an RF amplifier, lock-in amplifier, trans-impedance amplifier, or other amplifier configuration. Also different methods may be used in order to filter the excitation beam from the receiver beam before detection. PARS may use optical amplifiers to amplify detected light.

Figure 6A:
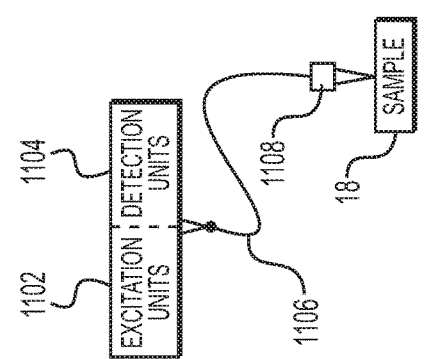
FIGS. 6A-6C are block diagrams of sensing systems in an endoscopy configuration, according to various embodiments.
Figure 6B:
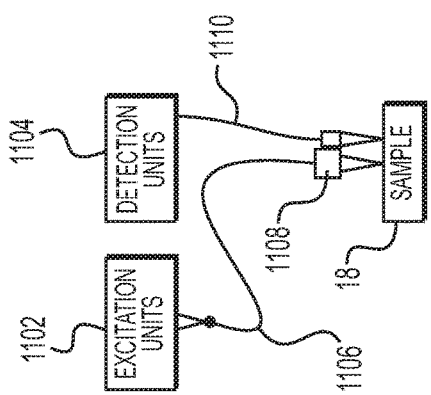
Figure 6C:
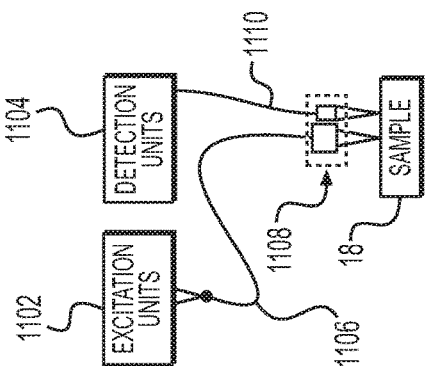

PARS may be used in many form factors, such as table top, handheld, surgical microscope, and endoscopy. Examples of endoscopy PARS are shown in FIGS. 6A, 6B and 6C with various arrangements of PARS excitation units 1102, PARS detection units 1104, fibre optics 1106 such as image-guide fibers, and lenses 1108 that focus the respective beams onto sample 18. When excitation and detection units 1102 and 1104 are separated, there may be a separate fiber 1110 provided, such as a single mode fiber.

A table top and handheld PARS may be constructed based on principles known in the art. The proposed PARS takes advantage of optical excitation and detection which can help to dramatically reduce the footprint of the system. The footprint of previous systems has been much too large to use the system in all but body surfaces. For endoscopic applications, the footprint of the ultrasound detector must be minimized to make the imaging catheter small and flexible enough to navigate through small orifices and vessels. The piezoelectric receivers are not ideal candidates for endoscopic applications as there is trade-off between the sensitivity and the size of the receiver. On the other hand for many invasive applications sterilisable or disposable catheters and a non-contact approach are necessary. The system may also be used as PARS endoscopy system with a potential footprint the size of an optical fiber, as both excitation and PARS beam can be coupled into a single mode fiber or image guide fiber.

Image-guide fibers (miniaturized fiber bundles with as many as 100,000 or more individual micrometer-sized strands in a single optical fiber with diameters ranging from 200 µm to 2 mm) may be used to transmit both focused light spots. The excitation beam may be scanned either at the distal end or proximal end of the fiber using one of the scanning methods mentioned before. However, the receiver beam may be scanned or be fixed. The scanned spot is transmitted via the image-guide fiber 1106 to the output end. Therefore, it may be used to directly contact the sample, or re-focused using an attached miniature GRIN lens 1108. In one example, C-scan photoacoustic images were obtained from the fiber image-guides using an external ultrasound transducer to collect photoacoustic signals. Using an edge-spread and Gaussian function, a resolution of approximately 7 µm was obtained using the image-guide fiber 1106. It is believed that a higher resolution may also be obtained with appropriate improvements to the setup and equipment used. This may be one possible embodiment of an endoscopic PARS device.

Endoscopic embodiments may also be constructed using single-mode fibers if, for example, the excitation and detection wavelengths are sufficiently close to each other, such as 532 nm and 637 nm. This would allow both wavelengths to propagate in single-modes in a highly compact probe when the fibers are, for example, only 250 microns in diameter.

Endoscopic PARS device embodiments may also be assembled using double-clad fibers. These fibers feature a single-mode core surrounded with a multi-mode core. This allows for highly dissimilar wavelengths, such as 532 nm and 1310 nm, to be combined into a single fiber while maintaining single-mode propagation for at least one of the wavelengths. As well, the double-clad fiber's multimode outer core may be used for increased return light collection as a means of directing collected light towards the optical detection components.

Figure 7:
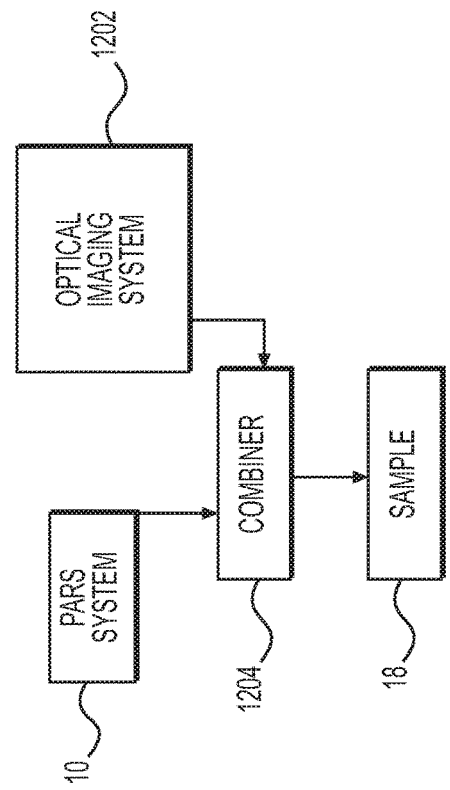
FIG. 7 is a block diagram of a sensing system integrated with another optical imaging system.

Various PARS embodiments may be combined with other imaging modalities such as fluorescence microscopy, two-photon and confocal fluorescence microscopy, Coherent-Anti-Raman-Stokes microscopy, Raman microscopy, Optical coherence tomography, other photoacoustic and ultrasound systems, etc. This may permit imaging of the microcirculation, blood oxygenation parameter imaging, and imaging of other molecularly-specific targets simultaneously, a potentially important task that is difficult to implement with only fluorescence based microscopy methods. An example of this is shown in FIG. 7, in which a PARS 10 is integrated with another optical imaging system 1202, where PARS 10 and the other optical imaging system 1202 are both connected to sample 18 by a combiner 1204.

Interferometric designs, such as common path interferometer (using specially designed interferometer objective lenses), Michelson interferometer, Fizeau interferometer, Ramsey interferometer, Sagnac interferometer, Fabry-Perot interferometer and Mach-Zehnder interferometer, may also be integrated with various embodiments of the disclosure.

A multi-wavelength visible laser source may also be implemented to generate photoacoustic signals for functional or structural imaging.

Polarization analyzers may be used to decompose detected light into respective polarization states. The light detected in each polarization state may provide information about ultrasound-tissue interaction.

Applications

It will be understood that the system described herein may be used in various ways, such as those purposes described in the prior art, and also may be used in other ways to take advantage of the aspects described above. A non-exhaustive list of applications is discussed below.

The system may be used for imaging angiogenesis for different pre-clinical tumor models.

The system may be used to image: (1) histological samples; (2) cell nuclei; (3) proteins; (4) cytochromes; (5) DNA; (6) RNA; and (7) lipids.

The system may also be used for clinical imaging of micro- and macro-circulation and pigmented cells, which may find use for applications such as in (1) the eye, potentially augmenting or replacing fluorescein angiography; (2) imaging dermatological lesions including melanoma, basal cell carcinoma, hemangioma, psoriasis, eczema, dermatitis, imaging Mohs surgery, imaging to verify tumor margin resections; (3) peripheral vascular disease; (4) diabetic and pressure ulcers; (5) burn imaging; (6) plastic surgery and microsurgery; (7) imaging of circulating tumor cells, especially melanoma cells; (8) imaging lymph node angiogenesis; (9) imaging response to photodynamic therapies including those with vascular ablative mechanisms; (10) imaging response to chemotherapeutics including anti-angiogenic drugs; (11) imaging response to radiotherapy.

The system may be useful in estimating oxygen saturation using multi-wavelength photoacoustic excitation and PARS detection and applications including: (1) estimating venous oxygen saturation where pulse oximetry cannot be used including estimating cerebrovenous oxygen saturation and central venous oxygen saturation. This could potentially replace catheterization procedures which can be risky, especially in small children and infants.

Oxygen flux and oxygen consumption may also be estimated by using PARS imaging to estimate oxygen saturation, and an auxiliary method to estimate blood flow in vessels flowing into and out of a region of tissue.

The system may also have some gastroenterological applications, such as imaging vascular beds and depth of invasion in Barrett's esophagus and colorectal cancers. Depth of invasion is key to prognosis and metabolic potential. Gastroenterological applications may be combined or piggy-backed off of a clinical endoscope and the miniaturized PARS may be designed either as a standalone endoscope or fit within the accessory channel of a clinical endoscope.

The system may have some surgical applications, such as functional imaging during brain surgery, use for assessment of internal bleeding and cauterization verification, imaging perfusion sufficiency of organs and organ transplants, imaging angiogenesis around islet transplants, imaging of skin-grafts, imaging of tissue scaffolds and biomaterials to evaluate vascularization and immune rejection, imaging to aid microsurgery, guidance to avoid cutting critical blood vessels and nerves.

Other examples of applications may include PARS imaging of contrast agents in clinical or pre-clinical applications; identification of sentinel lymph nodes; non- or minimally-invasive identification of tumors in lymph nodes; imaging of genetically-encoded reporters such as tyrosinase, chromoproteins, fluorescent proteins for pre-clinical or clinical molecular imaging applications; imaging actively or passively targeted optically absorbing nanoparticles for molecular imaging; and imaging of blood clots and potentially staging the age of the clots.

In this patent document, the word "comprising" is used in its non-limiting sense to mean that items following the word are included, but items not specifically mentioned are not excluded. A reference to an element by the indefinite article "a" does not exclude the possibility that more than one of the elements is present, unless the context clearly requires that there be one and only one of the elements.

The scope of the following claims should not be limited by the preferred embodiments set forth in the examples above and in the drawings, but should be given the broadest interpretation consistent with the description as a whole.

The invention claimed is:

1. A photon absorption remote sensing system (PARS) for imaging a subsurface structure in a sample, comprising:
   one or more laser sources configured to generate a plurality of excitation beams configured to generate signals in the sample at an excitation location;
   wherein the one or more laser sources are also configured to generate a plurality of interrogation beams incident on the sample at the excitation location, wherein a portion of the first interrogation beams returning from the sample is indicative of the generated signals;
   an optical system configured to focus the plurality of excitation beams at a first focal point and the plurality of interrogation beams at a second focal point, the first and second focal points being below the surface of the sample;
   a plurality of detectors each configured to detect the returning portion of at least one of the plurality of interrogation beams, wherein the plurality of detectors surround a reference point at the sample and/or aligned with the sample.

2. The PARS of claim 1, wherein the one or more wherein the one or more laser sources includes a plurality of laser sources.

3. The PARS of claim 1, wherein each of the plurality of excitation beams has a different wavelength.

4. The PARS of claim 3, wherein the plurality of excitation beams include:
   a near-infrared beam;
   a short-wave infrared beam;
   a UVC beam;
   a UVB beam;
   a UVA beam; and
   visible light.

5. The PARS of claim 1, wherein the plurality of excitation beams are configured to be delivered sequentially onto the sample.

6. The PARS of claim 1, wherein the plurality of excitation beams are configured to be delivered simultaneously onto the sample.

7. The PARS of claim 1, wherein the first and second focal points are at a depth below the surface of the sample that is from 50 nm to 8 mm.

8. The PARS of claim 1, wherein the PARS is used in one or more of the following applications:
   imaging histological samples;
   imaging cell nuclei;
   imaging proteins;
   imaging cytochromes;
   imaging DNA;
   imaging RNA;
   imaging lipids;
   imaging of blood oxygen saturation;
   imaging of tumor hypoxia;
   imaging of wound healing, burn diagnostics, or surgery;
   imaging of microcirculation;
   blood oxygenation parameter imaging;
   estimating blood flow in vessels flowing into and out of a region of tissue;
   imaging of molecularly-specific targets;
   imaging angiogenesis for pre-clinical tumor models;
   clinical imaging of micro- and macro-circulation and pigmented cells;
   imaging of the eye;
   augmenting or replacing fluorescein angiography;
   imaging dermatological lesions;
   imaging melanoma;
   imaging basal cell carcinoma;
   imaging hemangioma;
   imaging psoriasis;
   imaging eczema;
   imaging dermatitis;
   imaging Mohs surgery;
   imaging to verify tumor margin resections;
   imaging peripheral vascular disease;
   imaging diabetic and/or pressure ulcers;
   burn imaging;
   plastic surgery;
   microsurgery;
   imaging of circulating tumor cells;
   imaging melanoma cells;
   imaging lymph node angiogenesis;
   imaging response to photodynamic therapies;
   imaging response to photodynamic therapies having vascular ablative mechanisms;
   imaging response to chemotherapeutics;
   imaging response to anti-angiogenic drugs;
   imaging response to radiotherapy;
   estimating oxygen saturation using multi-wavelength photoacoustic excitation;
   estimating venous oxygen saturation where pulse oximetry cannot be used;

estimating cerebrovenous oxygen saturation and/or central venous oxygen saturation;
estimating oxygen flux and/or oxygen consumption;
imaging vascular beds and depth of invasion in Barrett's esophagus and/or colorectal cancers;
functional imaging during brain surgery;
assessment of internal bleeding and/or cauterization verification;
imaging perfusion sufficiency of organs and/or organ transplants;
imaging angiogenesis around islet transplants;
imaging of skin-grafts;
imaging of tissue scaffolds and/or biomaterials to evaluate vascularization and/or immune rejection;
imaging to aid microsurgery;
guidance to avoid cutting blood vessels and/or nerves;
imaging of contrast agents in clinical or pre-clinical applications;
identification of sentinel lymph nodes;
non- or minimally-invasive identification of tumors in lymph nodes;
imaging of genetically-encoded reporters, wherein the genetically-encoded reporters include tyrosinase, chromoproteins, and/or fluorescent proteins for pre-clinical or clinical molecular imaging applications;
imaging actively or passively targeted optically absorbing nanoparticles for molecular imaging;
imaging of blood clots; or
staging an age of blood clots.

9. A photon absorption remote sensing system (PARS) for imaging a subsurface structure in a sample, comprising:
one or more laser sources configured to generate at least one excitation beam configured to generate signals in the sample at an excitation location, wherein the at least one excitation beam is directed to the sample along a first path; and
wherein the one or more laser sources are also configured to generate at least one interrogation beam incident on the sample at the excitation location and directed to the sample along a second path that is angled and offset from the first path, at least one portion of the at least one interrogation beam returning from the sample that is indicative of the generated signals, wherein the returning portion of the at least one interrogation beam returns along a third path that is angled and offset from each of the first path and the second path; and
a first optical system configured to focus the at least one excitation beam at a first focal point;
a second optical system configured to focus the at least one interrogation beam at a second focal point, the first and second focal points being below the surface of the sample; and
at least one detector configured to detect at least one returning portion of the at least one interrogation beam.

10. The PARS of claim 9, wherein an angle between the first path and second path is substantially similar to an angle between the second path and the third path.

11. The PARS of claim 10, wherein the angle between the first path and the third path is substantially similar to an angle between the first path and the second path.

12. The PARS of claim 9, wherein the first and second focal points are at a depth below the surface of the sample that is from 50 nm to 8 mm.

13. The PARS of claim 9, wherein the PARS is used in one or more of the following applications:
imaging histological samples;
imaging cell nuclei;
imaging proteins;
imaging cytochromes;
imaging DNA;
imaging RNA;
imaging lipids;
imaging of blood oxygen saturation;
imaging of tumor hypoxia;
imaging of wound healing, burn diagnostics, or surgery;
imaging of microcirculation;
blood oxygenation parameter imaging;
estimating blood flow in vessels flowing into and out of a region of tissue;
imaging of molecularly-specific targets;
imaging angiogenesis for pre-clinical tumor models;
clinical imaging of micro- and macro-circulation and pigmented cells;
imaging of the eye;
augmenting or replacing fluorescein angiography;
imaging dermatological lesions;
imaging melanoma;
imaging basal cell carcinoma;
imaging hemangioma;
imaging psoriasis;
imaging eczema;
imaging dermatitis;
imaging Mohs surgery;
imaging to verify tumor margin resections;
imaging peripheral vascular disease;
imaging diabetic and/or pressure ulcers;
burn imaging;
plastic surgery;
microsurgery;
imaging of circulating tumor cells;
imaging melanoma cells;
imaging lymph node angiogenesis;
imaging response to photodynamic therapies;
imaging response to photodynamic therapies having vascular ablative mechanisms;
imaging response to chemotherapeutics;
imaging response to anti-angiogenic drugs;
imaging response to radiotherapy;
estimating oxygen saturation using multi-wavelength photoacoustic excitation;
estimating venous oxygen saturation where pulse oximetry cannot be used;
estimating cerebrovenous oxygen saturation and/or central venous oxygen saturation;
estimating oxygen flux and/or oxygen consumption;
imaging vascular beds and depth of invasion in Barrett's esophagus and/or colorectal cancers;
functional imaging during brain surgery;
assessment of internal bleeding and/or cauterization verification;
imaging perfusion sufficiency of organs and/or organ transplants;
imaging angiogenesis around islet transplants;
imaging of skin-grafts;
imaging of tissue scaffolds and/or biomaterials to evaluate vascularization and/or immune rejection;
imaging to aid microsurgery;
guidance to avoid cutting blood vessels and/or nerves;
imaging of contrast agents in clinical or pre-clinical applications;
identification of sentinel lymph nodes;
non- or minimally-invasive identification of tumors in lymph nodes;

imaging of genetically-encoded reporters, wherein the genetically-encoded reporters include tyrosinase, chromoproteins, and/or fluorescent proteins for pre-clinical or clinical molecular imaging applications;
imaging actively or passively targeted optically absorbing nanoparticles for molecular imaging;
imaging of blood clots; or
staging an age of blood clots.

14. A photon absorption remote sensing system (PARS) for imaging a subsurface structure in a sample, comprising:
one or more laser sources configured to generate at least one excitation beam configured to generate signals in the sample at an excitation location;
wherein the one or more laser sources are also configured to generate at least one interrogation beam incident on the sample at the excitation location, at least one portion of the at least one interrogation beam returning from the sample that is indicative of the generated signals;
an optical system configured to focus the at least one excitation beam at a first focal point and the at least one interrogation beam at a second focal point, the first and second focal points being below the surface of the sample; and
a polarizing modulation detector configured to detect a polarization modulation of the at least one returning portion, wherein an arrangement of the polarizing modulation detector, the optical system, and the one or more laser sources is configured such that the polarizing modulation detector detects only photons that have been modulated by the excitation laser.

15. The PARS of claim 14, wherein the first and second focal points are at a depth below the surface of the sample that is from 50 nm to 8 mm.

16. The PARS of claim 14, wherein the PARS is used in one or more of the following applications:
imaging histological samples;
imaging cell nuclei;
imaging proteins;
imaging cytochromes;
imaging DNA;
imaging RNA;
imaging lipids;
imaging of blood oxygen saturation;
imaging of tumor hypoxia;
imaging of wound healing, burn diagnostics, or surgery;
imaging of microcirculation;
blood oxygenation parameter imaging;
estimating blood flow in vessels flowing into and out of a region of tissue;
imaging of molecularly-specific targets;
imaging angiogenesis for pre-clinical tumor models;
clinical imaging of micro- and macro-circulation and pigmented cells;
imaging of the eye;
augmenting or replacing fluorescein angiography;
imaging dermatological lesions;
imaging melanoma;
imaging basal cell carcinoma;
imaging hemangioma;
imaging psoriasis;
imaging eczema;
imaging dermatitis;
imaging Mohs surgery;
imaging to verify tumor margin resections;
imaging peripheral vascular disease;
imaging diabetic and/or pressure ulcers;
burn imaging;
plastic surgery;
microsurgery;
imaging of circulating tumor cells;
imaging melanoma cells;
imaging lymph node angiogenesis;
imaging response to photodynamic therapies;
imaging response to photodynamic therapies having vascular ablative mechanisms;
imaging response to chemotherapeutics;
imaging response to anti-angiogenic drugs;
imaging response to radiotherapy;
estimating oxygen saturation using multi-wavelength photoacoustic excitation;
estimating venous oxygen saturation where pulse oximetry cannot be used;
estimating cerebrovenous oxygen saturation and/or central venous oxygen saturation;
estimating oxygen flux and/or oxygen consumption;
imaging vascular beds and depth of invasion in Barrett's esophagus and/or colorectal cancers;
functional imaging during brain surgery;
assessment of internal bleeding and/or cauterization verification;
imaging perfusion sufficiency of organs and/or organ transplants;
imaging angiogenesis around islet transplants;
imaging of skin-grafts;
imaging of tissue scaffolds and/or biomaterials to evaluate vascularization and/or immune rejection;
imaging to aid microsurgery;
guidance to avoid cutting blood vessels and/or nerves;
imaging of contrast agents in clinical or pre-clinical applications;
identification of sentinel lymph nodes;
non- or minimally-invasive identification of tumors in lymph nodes;
imaging of genetically-encoded reporters, wherein the genetically-encoded reporters include tyrosinase, chromoproteins, and/or fluorescent proteins for pre-clinical or clinical molecular imaging applications;
imaging actively or passively targeted optically absorbing nanoparticles for molecular imaging;
imaging of blood clots; or
staging an age of blood clots.

17. A photon absorption remote sensing system (PARS) for imaging a subsurface structure in a sample, comprising:
one or more laser sources configured to generate at least one excitation beam configured to generate signals in the sample at an excitation location;
wherein the one or more laser sources are also configured to generate at least one interrogation beam incident on the sample at the excitation location, at least one portion of the at least one interrogation beam returning from the sample that is indicative of the generated signals;
an optical system configured to focus the at least one excitation beam at a first focal point and the at least one interrogation beam at a second focal point, the first and second focal points being below the surface of the sample; and
a phase modulation detector configured to detect a phase modulation of the at least one returning portion, wherein an arrangement of the phase modulation detector, the optical system, and the one or more laser sources is configured such that the phase modulation detector detects only photons that have been modulated by the excitation laser.

18. The PARS of claim 17, wherein the first and second focal points are at a depth below the surface of the sample that is from 50 nm to 8 mm.

19. The PARS of claim 17, wherein the PARS is used in one or more of the following applications:
- imaging histological samples;
- imaging cell nuclei;
- imaging proteins;
- imaging cytochromes;
- imaging DNA;
- imaging RNA;
- imaging lipids;
- imaging of blood oxygen saturation;
- imaging of tumor hypoxia;
- imaging of wound healing, burn diagnostics, or surgery;
- imaging of microcirculation;
- blood oxygenation parameter imaging;
- estimating blood flow in vessels flowing into and out of a region of tissue;
- imaging of molecularly-specific targets;
- imaging angiogenesis for pre-clinical tumor models;
- clinical imaging of micro- and macro-circulation and pigmented cells;
- imaging of the eye;
- augmenting or replacing fluorescein angiography;
- imaging dermatological lesions;
- imaging melanoma;
- imaging basal cell carcinoma;
- imaging hemangioma;
- imaging psoriasis;
- imaging eczema;
- imaging dermatitis;
- imaging Mohs surgery;
- imaging to verify tumor margin resections;
- imaging peripheral vascular disease;
- imaging diabetic and/or pressure ulcers;
- burn imaging;
- plastic surgery;
- microsurgery;
- imaging of circulating tumor cells;
- imaging melanoma cells;
- imaging lymph node angiogenesis;
- imaging response to photodynamic therapies;
- imaging response to photodynamic therapies having vascular ablative mechanisms;
- imaging response to chemotherapeutics;
- imaging response to anti-angiogenic drugs;
- imaging response to radiotherapy;
- estimating oxygen saturation using multi-wavelength photoacoustic excitation;
- estimating venous oxygen saturation where pulse oximetry cannot be used;
- estimating cerebrovenous oxygen saturation and/or central venous oxygen saturation;
- estimating oxygen flux and/or oxygen consumption;
- imaging vascular beds and depth of invasion in Barrett's esophagus and/or colorectal cancers;
- functional imaging during brain surgery;
- assessment of internal bleeding and/or cauterization verification;
- imaging perfusion sufficiency of organs and/or organ transplants;
- imaging angiogenesis around islet transplants;
- imaging of skin-grafts;
- imaging of tissue scaffolds and/or biomaterials to evaluate vascularization and/or immune rejection;
- imaging to aid microsurgery;
- guidance to avoid cutting blood vessels and/or nerves;
- imaging of contrast agents in clinical or pre-clinical applications;
- identification of sentinel lymph nodes;
- non- or minimally-invasive identification of tumors in lymph nodes;
- imaging of genetically-encoded reporters, wherein the genetically-encoded reporters include tyrosinase, chromoproteins, and/or fluorescent proteins for pre-clinical or clinical molecular imaging applications;
- imaging actively or passively targeted optically absorbing nanoparticles for molecular imaging;
- imaging of blood clots; or
- staging an age of blood clots.

20. A photon absorption remote sensing system (PARS) for imaging a structure in a sample, comprising:
- one or more laser sources configured to generate at least one excitation beam configured to generate signals in the sample at an excitation location;
- wherein the one or more laser sources also are configured to generate at least one interrogation beam incident on the sample at the excitation location, at least one portion of the at least one interrogation beam returning from the sample that is indicative of the generated signals; and
- a detector configured to detect at least one light property of the at least one returning portion, wherein beam paths of the excitation beam, the interrogation beam, and the returning portion of the interrogation beam are distributed along an azimuth with respect to a plane of a surface of the sample, and wherein each beam path has, with respect to the plane, a congruent altitude angle in a range of 20 degrees to 90 degrees.

* * * * *

UNITED STATES PATENT AND TRADEMARK OFFICE
CERTIFICATE OF CORRECTION

| | |
|---|---|
| PATENT NO. | : 11,841,315 B2 |
| APPLICATION NO. | : 16/629371 |
| DATED | : December 12, 2023 |
| INVENTOR(S) | : Haji Reza et al. |

It is certified that error appears in the above-identified patent and that said Letters Patent is hereby corrected as shown below:

In the Claims

Column 19, Lines 63-64, in Claim 2, after "more" delete "wherein the one or more".

Column 26, Line 45 (approx.), in Claim 20, before "wherein" insert --an optical system configured to focus the plurality of excitation beams at a first focal point and the plurality of interrogation beams at a second focal point, the first and second focal points being below the surface of the sample;--.

Signed and Sealed this
Twelfth Day of March, 2024

Katherine Kelly Vidal
*Director of the United States Patent and Trademark Office*